(12) United States Patent
Genberg et al.

(10) Patent No.: US 9,603,859 B2
(45) Date of Patent: *Mar. 28, 2017

(54) METHODS AND PRODUCTS FOR INCREASING THE RATE OF HEALING OF TISSUE WOUNDS

(71) Applicants: Carl Genberg, Las Vegas, NV (US); Paul B. Savage, Mapleton, UT (US)

(72) Inventors: Carl Genberg, Las Vegas, NV (US); Paul B. Savage, Mapleton, UT (US)

(73) Assignee: BRIGHAM YOUNG UNIVERSITY, Provo, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/848,819

(22) Filed: Sep. 9, 2015

(65) Prior Publication Data

US 2015/0374720 A1 Dec. 31, 2015

Related U.S. Application Data

(63) Continuation-in-part of application No. 13/615,324, filed on Sep. 13, 2012, now Pat. No. 9,161,942.

(60) Provisional application No. 61/534,194, filed on Sep. 13, 2011.

(51) Int. Cl.
*A61K 31/575* (2006.01)

(52) U.S. Cl.
CPC .................................. *A61K 31/575* (2013.01)

(58) Field of Classification Search
CPC .... A61K 31/575; G06F 3/0416; G06F 3/0488
See application file for complete search history.

(56) References Cited

U.S. PATENT DOCUMENTS

| | | | |
|---|---|---|---|
| 4,661,341 A | 4/1987 | Benedict et al. | |
| 4,842,593 A | 6/1989 | Jordan et al. | |
| 4,865,855 A | 9/1989 | Hansen et al. | |
| 4,972,848 A | 11/1990 | Di Domenico | |
| 5,025,754 A | 6/1991 | Plyler | |
| 5,286,479 A | 2/1994 | Garlich et al. | |
| 5,310,545 A | 5/1994 | Eisen | |
| 5,356,630 A | 10/1994 | Laurencin et al. | |
| 5,380,839 A | 1/1995 | McCall et al. | |
| 5,552,057 A | 9/1996 | Hughes et al. | |
| 5,721,359 A | 2/1998 | Dunn et al. | |
| 6,117,332 A | 9/2000 | Hatch et al. | |
| 6,228,393 B1 | 5/2001 | DiCosmo et al. | |
| 6,350,738 B1 | 2/2002 | Savage et al. | |
| 6,486,148 B2 | 11/2002 | Savage et al. | |
| 6,562,318 B1 | 5/2003 | Filler | |
| 6,673,771 B1 | 1/2004 | Greene et al. | |
| 6,767,904 B2 | 7/2004 | Savage et al. | |
| 6,803,066 B2 | 10/2004 | Traeder | |
| 6,872,303 B2 | 3/2005 | Knapp et al. | |
| 6,939,376 B2 | 9/2005 | Shulze et al. | |
| 7,282,214 B2 | 10/2007 | Willcox et al. | |
| 7,381,439 B2 | 6/2008 | Hilgren et al. | |
| 7,598,234 B2 | 10/2009 | Savage et al. | |
| 7,659,061 B2 | 2/2010 | Hendl et al. | |
| 7,754,705 B2 | 7/2010 | Savage et al. | |
| 7,854,941 B2 | 12/2010 | Urban et al. | |
| 7,993,903 B2 | 8/2011 | Hayakawa et al. | |
| 8,211,879 B2 | 7/2012 | Savage et al. | |
| 8,529,681 B1 * | 9/2013 | Hibbs ....................... | C08F 2/48 |
| | | | 106/15.05 |
| 8,623,416 B2 | 1/2014 | Zasloff et al. | |
| 8,691,252 B2 | 4/2014 | Savage | |
| 8,784,857 B2 | 7/2014 | Savage | |
| 8,932,614 B2 | 1/2015 | Savage et al. | |
| 8,945,217 B2 | 2/2015 | Savage et al. | |
| 8,975,310 B2 | 3/2015 | Savage | |
| 9,155,746 B2 | 10/2015 | Genberg et al. | |
| 9,161,942 B2 | 10/2015 | Genberg et al. | |
| 2002/0091278 A1 | 7/2002 | Savage et al. | |
| 2003/0099717 A1 | 5/2003 | Cabrera | |
| 2004/0009227 A1 | 1/2004 | Yao | |
| 2004/0058974 A1 | 3/2004 | Courtney et al. | |
| 2004/0259445 A1 | 12/2004 | Hilfenhaus et al. | |
| 2005/0032765 A1 | 2/2005 | Savage et al. | |

(Continued)

FOREIGN PATENT DOCUMENTS

| CN | 101378761 | 3/2009 |
|---|---|---|
| CN | 102172356 | 9/2011 |

(Continued)

OTHER PUBLICATIONS

U.S. Appl. No. 13/783,007, filed Mar. 1, 2013, Savage.
U.S. Appl. No. 14/694,028, filed Apr. 23, 2015, Beus et al.
U.S. Appl. No. 14/830,356, filed Aug. 19, 2015, Savage.
U.S. Appl. No. 14/842,582, filed Sep. 1, 2015, Genberg et al.
U.S. Appl. No. 14/866,213, filed Sep. 25, 2015, Savage.
U.S. Appl. No. 14/873,013, filed Oct. 1, 2015, Savage et al.
U.S. Appl. No. 14/750,928, filed Jun. 25, 2015, Genberg et al.
U.S. Appl. No. 14/875,953, filed Oct. 6, 2015, Savage.
U.S. Appl. No. 14/926,738, filed Oct. 29, 2015, Vazquez et al.
Alhanout K et al: "Squalamine as an example of a new potent antimicrobial agents class: a critical review.", Current Medicinal Chemistry 2010, vol. 17, No. 32, 2010, pp. 3909-3917.
Atiq-Ur-Rehman Li C et al: "Preparation of Amino Acid-Appended Cholic Acid Derivatives as Sensitizers of Gram-Negative Bacteria", Tetrahedron Letters, Elsevier, Amsterdam, NL, vol. 40, No. 10, Mar. 5, 1999 (Mar. 5, 1999), pp. 1865-1868, XP004155984, ISSN: 0040-4039, DOI: 10.1016/S0040-4039(99)00075-1.

(Continued)

*Primary Examiner* — Snigdha Maewall
(74) *Attorney, Agent, or Firm* — Workman Nydegger

(57) ABSTRACT

Disclosed are methods for increasing the rate of healing of a tissue wound by administering a composition including a therapeutically effective amount of at least one cationic steroid antimicrobial (CSA). Also disclosed herein are methods of promoting wound healing in a subject in need of such promotion, comprising administering a composition comprising a therapeutically effective amount of at least one CSA. Additionally, disclosed herein are compounds and compositions comprising at least one CSA, or a pharmaceutically acceptable salt thereof, for use in the treatment of a tissue wound. Kits comprising such compositions and instructions on such methods are also contemplated herein.

29 Claims, No Drawings

(56) References Cited

U.S. PATENT DOCUMENTS

| | | | |
|---|---|---|---|
| 2005/0075321 A1 | 4/2005 | Ahlem et al. | |
| 2005/0244468 A1 | 11/2005 | Huang et al. | |
| 2005/0267051 A1 | 12/2005 | Lee et al. | |
| 2006/0062742 A1 | 3/2006 | Davis et al. | |
| 2006/0269485 A1 | 11/2006 | Friedman et al. | |
| 2007/0106393 A1 | 5/2007 | Miles et al. | |
| 2007/0190066 A1* | 8/2007 | Savage | A61K 31/575 424/159.1 |
| 2007/0190067 A1 | 8/2007 | Savage et al. | |
| 2007/0190558 A1 | 8/2007 | Savage et al. | |
| 2008/0174035 A1 | 7/2008 | Winterton | |
| 2008/0188819 A1 | 8/2008 | Kloke et al. | |
| 2009/0016973 A1 | 1/2009 | Ratcliff et al. | |
| 2009/0054295 A1 | 2/2009 | Vicari et al. | |
| 2009/0068122 A1 | 3/2009 | Pilch et al. | |
| 2009/0324517 A1 | 12/2009 | Kline | |
| 2010/0330086 A1 | 12/2010 | Savage et al. | |
| 2011/0091376 A1 | 4/2011 | Savage et al. | |
| 2011/0123624 A1 | 5/2011 | Zasloff | |
| 2012/0088733 A1* | 4/2012 | Kim | A61K 38/10 514/18.6 |
| 2012/0107382 A1 | 5/2012 | Savage et al. | |
| 2013/0022651 A1 | 1/2013 | Savage | |
| 2013/0236619 A1 | 9/2013 | Savage | |
| 2013/0280312 A1 | 10/2013 | De Szalay | |
| 2013/0280391 A1 | 10/2013 | Savage | |
| 2014/0107090 A1 | 4/2014 | Beus et al. | |
| 2014/0194401 A1 | 7/2014 | Genberg et al. | |
| 2014/0271761 A1 | 9/2014 | Savage et al. | |
| 2014/0274913 A1 | 9/2014 | Savage et al. | |
| 2014/0315873 A1 | 10/2014 | Beus et al. | |
| 2014/0336131 A1 | 11/2014 | Savage et al. | |
| 2014/0363780 A1 | 12/2014 | Vazquez et al. | |
| 2014/0369941 A1 | 12/2014 | Vazquez et al. | |
| 2015/0093423 A1 | 4/2015 | Savage et al. | |
| 2015/0110767 A1 | 4/2015 | Savage et al. | |
| 2015/0140063 A1 | 5/2015 | Savage | |
| 2015/0203527 A1 | 7/2015 | Savage | |
| 2015/0239928 A1 | 8/2015 | Savage | |
| 2015/0258121 A1 | 9/2015 | Darien et al. | |
| 2015/0258122 A1 | 9/2015 | Beus et al. | |
| 2015/0258123 A1 | 9/2015 | Savage et al. | |

FOREIGN PATENT DOCUMENTS

| | | |
|---|---|---|
| EP | 0341951 | 11/1989 |
| EP | 1208844 | 5/2002 |
| JP | 02014741 | 1/1990 |
| JP | 06153779 | 6/1994 |
| JP | 07501826 | 2/1995 |
| JP | 09248454 | 9/1997 |
| JP | 2002505292 | 2/2002 |
| JP | 2002255771 | 9/2002 |
| JP | 2002534532 | 10/2002 |
| JP | 2002538093 | 11/2002 |
| JP | 2004506645 | 3/2004 |
| JP | 2010533051 | 10/2010 |
| JP | 2010538074 | 12/2010 |
| JP | 2011527702 | 11/2011 |
| JP | 2014500741 | 1/2014 |
| WO | WO 9524415 | 9/1995 |
| WO | WO 9944616 | 9/1999 |
| WO | WO 0042058 | 7/2000 |
| WO | WO 0214342 | 2/2002 |
| WO | WO 02067979 | 9/2002 |
| WO | WO03015757 | 2/2003 |
| WO | WO03090799 | 11/2003 |
| WO | WO2004082588 | 9/2004 |
| WO | WO2004112852 | 12/2004 |
| WO | WO2007089903 | 8/2007 |
| WO | WO2007089906 | 8/2007 |
| WO | WO2007089907 | 8/2007 |
| WO | WO2007134176 | 11/2007 |
| WO | WO2008038965 | 4/2009 |
| WO | WO2009079066 | 6/2009 |
| WO | WO2010006192 | 1/2010 |
| WO | WO2010036427 | 4/2010 |
| WO | WO2010062562 | 6/2011 |
| WO | WO2011066260 | 6/2011 |
| WO | WO2011109704 | 9/2011 |
| WO | WO2012061651 | 5/2012 |
| WO | WO2013029055 | 2/2013 |
| WO | WO2013029059 | 2/2013 |
| WO | WO2013109236 | 7/2013 |

OTHER PUBLICATIONS

Berge et al., "Pharmaceutical Salts", Journal of Pharmaceutical Sciences, Jan. 1977, vol. 66, No. 1, pp. 1-19.

Bridot et al., "Hybrid Gadolinium Oxide Nanoparticles: Multimodal Contrast Agents for in Vivo Imaging", Journal of American Chemical Society, vol. 129, No. 16, pp. 5076-5084, Mar. 31, 2007.

Britton et al, "Imaging bacterial infection with 99mTc-ciprofloxacin (Infection)", Journal of Clinical Pathology, vol. 55, pp. 817-823, Apr. 6, 2015.

Bucki et al., "Salivary mucins inhibit antibacterial activity of the cathelicidin-derived LL-37 peptide but not the cationic steroid CSA-13", Journal of Antimicrobial Chemotherapy (2008) 62: 329-335, 7 pages.

Chin et al, "Antimicrobial Activities of Ceragenins against Clinical Isolates of Resistant *Staphylococcus aureas*", Antimicrobial Agents and Chemotherapy, vol. 51, No. 4, Apr. 2007, p. 1268-1273.

Chunhong, et al., "Antimicrobial Activities of Amine- and Guanidine-functionalized Cholic Acid Derivatives", Antimicrobial Agents and Chemotherapy, American Society for Microbiology, Washington DC, US, vol. 43, No. 6, Jun. 1999, pp. 1347-1349.

Clara et al., "Preclinical evaluation of magainin-A as a contraceptive antimicrobial agent", Fertility and Sterility 81 (5), pp. 1357-1365, 2004.

Ding, et al., "Origins of cell selectivity of cationic steroid antibiotics", Journal of American Chemical Society, Oct. 2004, pp. 13642-13648.

Fritsch et al, "In Vitro Activity of Nine Developmental Cationic Steroid Compounds (Ceragenins) against Clinical Isolates of Clostridium difficile", The 46th Interscience Conference on Antimicrobial Agents and Chemotherapy, Sep. 27, 2006, pp. 1-1.

Guan et al: "Preparation and Characterization of Cholic Acid-Derived Antimicrobial Agents with Controlled Stabilities", Organic Letters, American Chemical Society, US, vol. 2, No. 18, Sep. 7, 2000 (Sep. 7, 2000), pp. 2837-2840.

Guan et al: "Supporting Information: Preparation and Characterization of Cholic Acid-Derived Antimicrobial Agents with Controlled Stabilities", Organic Letters, Aug. 17, 2000 (Aug. 17, 2000), pp. 1-7, XP55017313, Retrieved from the Internet: URL:http://pubs.acs.org/doi/suppl/10.1021/ol0062704/suppl file/ol0062704 sl.pdf.

Howell et al., "Ceragenins: A 1-18, class of Antiviral Compounds to Treat Orthopox Infections", Journal of Investigative Dermatology, vol. 129, No. 11, Jun. 11, 2009, pp. 2688-2675.

Isogai E et al: "Ceragenin CSA-13 exhibits antimicrobial activity against cariogenic and periodontopathic bacteria", Oral Microbiology and Immunology, vol. 24, No. 2, Apr. 2009 (Apr. 2009), pp. 170-172.

International Search Report for PCT Application No. PCT/US2009/047485 dated Feb. 17, 2010.

International Search Report for PCT Application No. PCT/US2011/059225 dated Jan. 31, 2012.

International Search Report for PCT Application No. PCT/US2012/047750, dated Oct. 5, 2012.

International Search Report for PCT Application No. PCT/US2012/055244 dated Dec. 5, 2012.

International Search Report for PCT Application No. PCT/US2012/055248 dated Feb. 14, 2013.

International Search Report for PCT Application No. PCT/US2013/038090, Mailed Date: Jul. 24, 2013.

International Search Report for PCT Application No. PCT/US2014/034986 dated Aug. 28, 2014.

(56) References Cited

OTHER PUBLICATIONS

International Search Report for PCT Application No. PCT/US2013/065510 dated Apr. 30, 2015.
International Search Report for PCT Application No. PCT/US2015/020166 dated Sep. 2, 2015.
International Search Report for PCT Application No. PCT/US2015/038029 dated Sep. 29, 2015.
Lai, et al., "Controlled Released of a Bactericidal Ceragenin-Polymer Conjugate", Sep. 27, 2006, p. 1, 46th Annual Interscience Conference on Antimicrobial Agents and Chemotherapy.
Leszczynska et al., "Potential of ceragenin CSA-13 and its mixture with pluronic F-127 as treatment of topical bacterial infections", Journal of Applied Microbiology, vol. 110, No. 1, Oct. 21, 2010, pp. 229-238.
Perry et al., "Assessing peri-implant tissue infection prevention in a percutaneous model", Journal of Biomedical Materials Research Part B: Applied Biomaterials, vol. 02B, Nov. 19, 2009, pp. 397-408.
Pitten F-A, et al., "Efficacy of Cetylpyridinium Chloride Used as Oropharyngeal Antiseptic" Arzenimittel Forschung. Drug Research, ECV Editio Cantor Verlag, Aulendorf, DE, vol. 51, No. 7, Jan. 1, 2001, pp. 588-595.
Savage, et al., "Antibacterial Activities of Thin Films Containing Ceragenins", Microbial Surfaces: Structure, Interactions and Reactivity, ACS, May 30, 2008, pp. 65-78.
Paul B. Savage, et al: "Antibacterial Properties of cationic steroid antibiotics", FEMS Microbiology Letters, vol. 217, Nov. 2002, pp. 1-7.
Savage et al, "Thin Films Containing Ceragenins Prevent Biofilm Formation on Endotracheal Tubes", 9$^{th}$ International Federation of Infection Control Congress, Oct. 14, 2008, pp. 1-1.
P. B. Savage, et al., "Use of a Ceragenin-Based Coating to Prevent Bacterial Colonization of Urinary Catheters", 48th Annual Interscience Conference on Anti-Microbial Agents & Chemotherapy, Oct. 26, 2008, pp. 1-1.

Shi et al., "Multi-center randomized double-blind clinical trial on efficacy of a mouthwash containing 0.1% cetylpiridinium chloride on gingivitis and plaque and its safety", Chinese Journal of Evidence-Based Medicine (Sep. 2003, vol. 3, No. 3, pp. 171-177).
Sinclair et al., "Development of a broad spectrum polymer-released antimicrobial coating for the prevention of resistant strain bacterial infections", Journal of Biomedical Materials Research Part A, vol. 100A, No. 10, May 24, 2012, pp. 2732-2738.
Steeneveld et al., "Cow-specific treatment of clinical mastitis: an economic approach", Journal of Dairy Science vol. 94, Jan. 2011, pp. 174-188.
Suzuki et al., "Molecular Genetics of Plant Sterol Backbone Synthesis", 2007; Lipids; 42: 47-54.
Van Bambeke et al: "The bacterial envelope as a target for novel anti-MRSA antibiotics", Trends in Pharmacological Sciences, Elsevier, Haywarth, GB, vol. 29, No. 3, Feb. 11, 2008 (Feb. 11, 2008), pp. 124-134.
Van Den Bogaard et al., "Antibiotic Usage in Animals: Impact on Bacterial Resistance and Public Health"; 1999; Drugs; 58 (4): 589-607.
Xin-Zhong Lai et al., "Ceragenins: Cholic Acid-Based Mimics of Antimicrobial peptides", Account of Chemical Research vol. 41, No. 10, Oct. 21, 2008, pp. 1233-1240.
Yin, et al., "Antiangiogenic Treatment Delays Chondrocyte Maturation and Cone Formation During Lim Skeletogenesis", Journal of Bone and Mineral Research, American Society for Bone and Mineral Research, New York, NY, US, vol. 17, No. 1, Jan. 1, 2002.
Zanger et al., "Structure-Activity Relationship and Drug Design", Remington's Pharmaceutical Sciences, Chapter 27, 16th Edition, 1980, pp. 420-425.
U.S. Appl. No. 13/615,324, filed Sep. 13, 2012, Office Action dated Jan. 30, 2014.
U.S. Appl. No. 13/615,324, filed Sep. 13, 2012, Final Office Action dated Sep. 24, 2014.
U.S. Appl. No. 13/615,324, filed Sep. 13, 2012, Notice of Allowance dated Jun. 10, 2015.

* cited by examiner

METHODS AND PRODUCTS FOR INCREASING THE RATE OF HEALING OF TISSUE WOUNDS

CROSS REFERENCE TO RELATED APPLICATION

This application is a continuation-in-part of U.S. patent application Ser. No. 13/615,324, filed Sep. 13, 2012, which claims the benefit of U.S. Provisional Patent Application No. 61/534,194, filed Sep. 13, 2011, the disclosures of which are incorporated herein in their entirety.

BACKGROUND OF THE INVENTION

1. Field of the Invention

This invention relates to compositions and methods for increasing the rate of healing of tissue wounds in animals using cationic steroid antimicrobials (CSAs).

2. Relevant Technology

Wound healing is the complex and dynamic process of self-repair to restore cellular structures and tissue layers after an injury has occurred. The human wound healing process is divided into three distinct phases: the inflammatory phase, the proliferative phase, and the remodeling phase. The wound healing process may be further broken down beyond the three broad phases to a complex and coordinated series of biochemical events that include chemotaxis, phagocytosis, neocollagenesis, collagen degradation, and collagen remodeling to repair the damage. In addition, angiogenesis, epithelization, and the production of new glycosaminoglycans (GAGs) and proteoglycans are vital to the wound healing process. The culmination of these biological processes results in the replacement of normal skin structures with fibroblastic mediated scar tissue.

Prior to the initiation of the inflammatory phase, the clotting cascade begins to stop blood loss via clotting. Once clotting has begun, various soluble factors, including chemokines and cytokines, are released to attract cells to the site of injury. Growth factors, which are cytokines released by platelets, stimulate cells to accelerate their rate of division leading to increased healing rates. Platelets also release other proinflammatory factors like serotonin, bradykinin, prostaglandins, prostacyclins, thromboxane, and histamine, which serve a number of purposes, including to increase cell proliferation and migration to the area and to cause blood vessels to become dilated and porous.

The inflammation phase can be further broken down into four biochemical processes. First, immediately after a blood vessel is breached, ruptured cell membranes release inflammatory factors like thromboxanes and prostaglandins that result in vasoconstriction to prevent blood loss and to collect inflammatory cells and factors. Second, polymorphonuclear neutrophils (PMNs) arrive at the wound site, phagocytose debris and bacteria. Neutrophils also cleanse the wound by secreting proteases that break down damaged tissue. Third, neutrophils cleanse the injured area via the phagocytosis of debris, bacteria, neutrophils, damaged cells and tissue, and any other foreign cells or material. Macrophages also secrete a number of factors that push wound healing toward the next phase. Finally, inflammation dies down, fewer inflammatory factors are secreted, existing ones are broken down, and numbers of neutrophils and macrophages are reduced at the wound site.

The proliferative phase begins with the arrival of fibroblasts at the wound site, marking the onset of the proliferative phase, which biologically begins with angiogenesis. Angiogenesis or neovascularization is the process which occurs concurrently with fibroblast proliferation when endothelial cells migrate to the area of the wound. Fibroplasia and granulation begin during angiogenesis as a result of fibroblast recruitment and extracellular matrix formation. Then collagen and fibronectin are deposited by the fibroblast at the site of tissue granulation. Once collagen deposition has occurred, epithelialization takes place as a result of the presence of keratinocytes arriving at the newly deposited extracellular matrix. The final step in the proliferative phase is contraction, which requires the presence of neomyoblasts to connect the scar tissue to the surrounding healthy tissue and to pull the edges of the scar tissue together, restoring tensile strength to the skin surrounding the previously injured area.

A need exists to develop compositions and methods to enhance wound healing.

BRIEF SUMMARY

Disclosed herein are methods and compositions for treating a wound in a subject by increasing the rate of healing. The increased rate of healing is achieved using a cationic steroidal antimicrobial (CSA) compound. The CSA compounds include a sterol backbone and a plurality of cationic groups attached thereto.

The treatment of tissue wounds with CSAs has the surprising and unexpected result of increasing the rate of wound healing. Experimental data indicates that the increased rate of wound healing is distinct from the known anti-microbial effects of CSAs. When applied to wound sites in living subjects, the CSA compounds described herein have a profound and surprising effect on the rate of wound healing. The increased rates of healing is in many cases several times faster than healing rates using traditional antimicrobials. Studies indicate that this increase in wound healing is at least in part distinct from antimicrobial benefits. CSAs have been found to increase the rate of healing even in wounds where antimicrobial load is very low or in cases where infection is not an issue.

The increased rate of healing results in healthier and more natural tissue formation as compared to treatments with traditional antimicrobial compounds. The mechanism of action for the increased rate of healing is presently being studied. While the present invention is not limited to any particular mechanism, it is believed that the increased rate of tissue healing is caused by increases in fibroblastic migration and enhanced epithelial growth factors at the wound site. Subjects have also exhibited a significantly reduced sensitivity to pain. These benefits are unexpected for CSAs, which were thought to only be active against foreign microbes.

In some embodiments, a method is described for increasing the rate of wound healing in a subject. The method includes (i) providing a tissue treatment composition including a cationic steroidal anti-microbial (CSA) compound, the CSA compound including a steroidal group and a plurality of cationic groups attached thereto; (ii) identifying a subject in need of accelerated healing of a tissue wound; and (iii) contacting the tissue wound with the tissue treatment composition to increase the rate of healing thereof.

In some embodiments, the invention relates to a CSA for use in a novel method of treating wounds. In particular, the invention relates to a pharmaceutically acceptable CSA compound having a sterol backbone and a plurality of cationic groups attached thereto, wherein the CSA compound is for use in increasing the rate of wound healing in a subject.

In some embodiments, the CSA is a compound of Formula (V) or a pharmaceutically acceptable salt thereof:

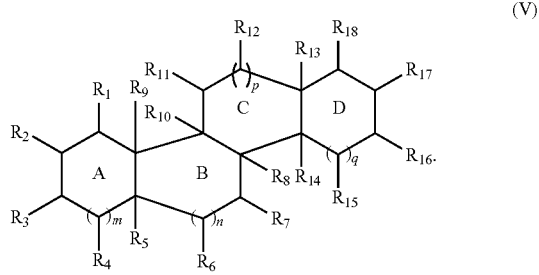

In some embodiments, the CSA, or a pharmaceutically acceptable salt thereof, is selected from the compound of Formula (I):

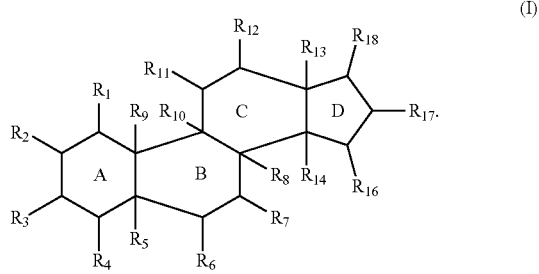

In some embodiments, the CSA, or a pharmaceutically acceptable salt thereof, is selected from the compound of Formula (Ia):

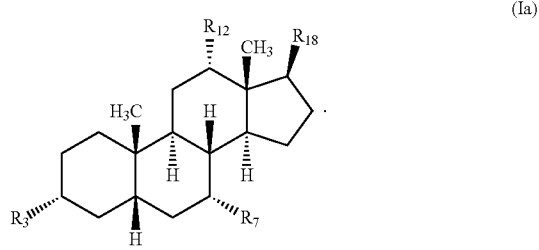

In some embodiments rings A, B, C, and D are independently saturated, or are fully or partially unsaturated, provided that at least two of rings A, B, C, and D are saturated; m, n, p, and q are independently 0 or 1; $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted alkyl, a substituted or unsubstituted hydroxyalkyl, a substituted or unsubstituted alkyloxyalkyl, a substituted or unsubstituted alkylcarboxyalkyl, a substituted or unsubstituted alkylaminoalkyl, a substituted or unsubstituted alkylaminoalkylamino, a substituted or unsubstituted alkylaminoalkylaminoalkylamino, a substituted or unsubstituted aminoalkyl, a substituted or unsubstituted aryl, a substituted or unsubstituted arylaminoalkyl, a substituted or unsubstituted haloalkyl, a substituted or unsubstituted alkenyl, a substituted or unsubstituted alkynyl, oxo, a linking group attached to a second steroid, a substituted or unsubstituted aminoalkyloxy, a substituted or unsubstituted aminoalkyloxyalkyl, a substituted or unsubstituted aminoalkylcarboxy, a substituted or unsubstituted aminoalkylaminocarbonyl, a substituted or unsubstituted aminoalkylcarboxamido, a substituted or unsubstituted di(alkyl)aminoalkyl, a substituted or unsubstituted C-carboxyalkyl, $H_2N$—$HC(Q_5)$-$C(O)$—$O$—, $H_2N$—$HC(Q_5)$-$C(O)$—$N(H)$—, a substituted or unsubstituted azidoalkyloxy, a substituted or unsubstituted cyanoalkyloxy, P.G.-HN—$HC(Q_5)$-$C(O)$—$O$—, a substituted or unsubstituted guanidinoalkyloxy, a substituted or unsubstituted quaternary ammonium alkylcarboxy, and a substituted or unsubstituted guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted alkyl, a substituted or unsubstituted hydroxyalkyl, a substituted or unsubstituted alkyloxyalkyl, a substituted or unsubstituted aminoalkyl, a substituted or unsubstituted aryl, a substituted or unsubstituted haloalkyl, a substituted or unsubstituted alkenyl, a substituted or unsubstituted alkynyl, oxo, a linking group attached to a second steroid, a substituted or unsubstituted aminoalkyloxy, a substituted or unsubstituted aminoalkylcarboxy, a substituted or unsubstituted aminoalkylaminocarbonyl, a substituted or unsubstituted di(alkyl)aminoalkyl, a substituted or unsubstituted C-carboxyalkyl, $H_2N$—$HC(Q_5)$-$C(O)$—$O$—, $H_2N$—$HC(Q_5)$-$C(O)$—$N(H)$—, azidoalkyloxy, cyanoalkyloxy, P.G.-HN—$HC(Q_5)$-$C(O)$—$O$—, guanidinoalkyloxy, and guanidinoalkylcarboxy, where $Q_5$ is a side chain of any amino acid, P.G. is an amino protecting group, provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted aminoalkyl, a substituted or unsubstituted aminoalkyloxy, a substituted or unsubstituted alkylcarboxyalkyl, a substituted or unsubstituted alkylaminoalkylamino, a substituted or unsubstituted alkylaminoalkylaminoalkylamino, a substituted or unsubstituted aminoalkylcarboxy, a substituted or unsubstituted arylaminoalkyl, a substituted or unsubstituted aminoalkyloxyaminoalkylaminocarbonyl, a substituted or unsubstituted aminoalkylaminocarbonyl, a substituted or unsubstituted aminoalkylcarboxyamido, a quaternary ammonium alkylcarboxy, a substituted or unsubstituted di(alkyl)aminoalkyl, a substituted or unsubstituted C-carboxyalkyl, $H_2N$—$HC(Q_5)$-$C(O)$—$O$—, $H_2N$—$HC(Q_5)$-$C(O)$—$N(H)$—, azidoalkyloxy, cyanoalkyloxy, P.G.-HN—$HC(Q_5)$-$C(O)$—$O$—, a substituted or unsubstituted guanidinoalkyloxy, and a substituted or unsubstituted guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted $(C_1$-$C_{18})$ alkyl, a substituted or unsubstituted $(C_1$-$C_{18})$ hydroxyalkyl, a substituted or unsubstituted $(C_1$-$C_{18})$ alkyloxy-$(C_1$-$C_{18})$ alkyl, a substituted or unsubstituted $(C_1$-$C_{18})$ alkylcarboxy-$(C_1$-$C_{18})$ alkyl, a substituted or unsubstituted $(C_1$-$C_{18})$ alkylamino-$(C_1$-$C_{18})$alkyl, a substituted or unsubstituted $(C_1$-$C_{18})$ alkylamino-$(C_1$-$C_{18})$ alkylamino, a substituted or unsubstituted $(C_1$-$C_{18})$ alkylamino-$(C_1$-$C_{18})$ alkylamino-$(C_1$-$C_{18})$ alkylamino, a substituted or unsubstituted $(C_1$-$C_{18})$ aminoalkyl, a substituted or unsubstituted aryl, a substituted or unsubstituted arylamino-($C_1$-$C_{18}$) alkyl, a substituted or unsubstituted ($C_1$-$C_{18}$) haloalkyl, a substituted or unsubstituted $C_2$-$C_6$ alkenyl, a substituted or unsubstituted $C_2$-$C_6$ alkynyl, oxo, a linking group attached to a second steroid, a substituted or unsubstituted ($C_1$-$C_{18}$) aminoalkyloxy, a substituted or unsubstituted ($C_1$-$C_{18}$) aminoalkyloxy-($C_1$-$C_{18}$) alkyl, a substituted or unsubstituted ($C_1$-$C_{18}$) aminoalkylcarboxy, a substituted or unsubstituted ($C_1$-$C_{18}$) aminoalkylaminocarbonyl, a substituted or unsubstituted ($C_1$-$C_{18}$) aminoalkylcarboxamido, a substituted or unsubstituted di($C_1$-$C_{18}$ alkyl)aminoalkyl, a substituted or unsubstituted C-carboxy($C_1$-$C_{18}$)alkyl, $H_2N$—HC($Q_5$)-C(O)—O—, $H_2N$—HC($Q_5$)-C(O)—N(H)—, a substituted or unsubstituted ($C_1$-$C_{18}$) azidoalkyloxy, a substituted or unsubstituted ($C_1$-$C_{18}$) cyanoalkyloxy, P.G.-HN—HC($Q_5$)-C(O)—O—, a substituted or unsubstituted ($C_1$-$C_{18}$) guanidinoalkyloxy, a substituted or unsubstituted ($C_1$-$C_{18}$) quaternary ammonium alkylcarboxy, and a substituted or unsubstituted ($C_1$-$C_{18}$) guanidinoalkyl carboxy, where $Q_5$ is a side chain of any amino acid (including a side chain of glycine, i.e., H), and P.G. is an amino protecting group; $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted ($C_1$-$C_{18}$) alkyl, a substituted or unsubstituted ($C_1$-$C_{18}$) hydroxyalkyl, a substituted or unsubstituted ($C_1$-$C_{18}$) alkyloxy-($C_1$-$C_{18}$) alkyl, a substituted or unsubstituted ($C_1$-$C_{18}$) aminoalkyl, a substituted or unsubstituted aryl, a substituted or unsubstituted ($C_1$-$C_{18}$) haloalkyl, a substituted or unsubstituted ($C_2$-$C_6$) alkenyl, a substituted or unsubstituted ($C_2$-$C_6$) alkynyl, oxo, a linking group attached to a second steroid, a substituted or unsubstituted ($C_1$-$C_{18}$) aminoalkyloxy, a substituted or unsubstituted ($C_1$-$C_{18}$) aminoalkylcarboxy, a substituted or unsubstituted ($C_1$-$C_{18}$) aminoalkylaminocarbonyl, a substituted or unsubstituted di($C_1$-$C_{18}$ alkyl)aminoalkyl, a substituted or unsubstituted C-carboxy($C_1$-$C_{18}$)alkyl, $H_2N$—HC($Q_5$)-C(O)—O—, $H_2N$—HC($Q_5$)-C(O)—N(H)—, a substituted or unsubstituted ($C_1$-$C_{18}$) azidoalkyloxy, a substituted or unsubstituted ($C_1$-$C_{18}$) cyanoalkyloxy, P.G.-HN—HC($Q_5$)-C(O)—O—, a substituted or unsubstituted ($C_1$-$C_{18}$) guanidinoalkyloxy, and ($C_1$-$C_{18}$) guanidinoalkylcarboxy, where $Q_5$ is a side chain of any amino acid, and P.G. is an amino protecting group; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted ($C_1$-$C_{18}$) aminoalkyl, a substituted or unsubstituted ($C_1$-$C_{18}$) aminoalkyloxy, a substituted or unsubstituted ($C_1$-$C_{18}$) alkylcarboxy-($C_1$-$C_{18}$) alkyl, a substituted or unsubstituted ($C_1$-$C_{18}$) alkylamino-($C_1$-$C_{18}$) alkylamino, a substituted or unsubstituted ($C_1$-$C_{18}$) alkylamino-($C_1$-$C_{18}$) alkylamino ($C_1$-$C_{18}$) alkylamino, a substituted or unsubstituted ($C_1$-$C_{18}$) aminoalkylcarboxy, a substituted or unsubstituted arylamino ($C_1$-$C_{18}$) alkyl, a substituted or unsubstituted ($C_1$-$C_{18}$) aminoalkyloxy ($C_1$-$C_{18}$) aminoalkylaminocarbonyl, a substituted or unsubstituted ($C_1$-$C_{18}$) aminoalkylaminocarbonyl, a substituted or unsubstituted ($C_1$-$C_{18}$) aminoalkylcarboxamido, a substituted or unsubstituted ($C_1$-$C_{18}$) quaternary ammonium alkylcarboxy, a substituted or unsubstituted di($C_1$-$C_{18}$ alkyl)aminoalkyl, a substituted or unsubstituted C-carboxy($C_1$-$C_{18}$)alkyl, $H_2N$—HC($Q_5$)-C(O)—O—, $H_2N$—HC($Q_5$)-C(O)—N(H)—, a substituted or unsubstituted ($C_1$-$C_{18}$) azidoalkyloxy, a substituted or unsubstituted ($C_1$-$C_{18}$) cyanoalkyloxy, P.G.-HN—HC($Q_5$)-C(O)—O—, a substituted or unsubstituted ($C_1$-$C_{18}$) guanidinoalkyloxy, and a substituted or unsubstituted ($C_1$-$C_{18}$) guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, ($C_1$-$C_{18}$) unsubstituted ($C_1$-$C_{18}$) aminoalkylaminocarbonyl, an unsubstituted aminoalkylcarboxamido, an unsubstituted di($C_1$-$C_{18}$ alkyl)aminoalkyl, a substituted or unsubstituted C-carboxy($C_1$-$C_{18}$)alkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy; $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$) alkyl, ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted ($C_1$-$C_{18}$ alkyl)aminoalkyl, a substituted or unsubstituted C-carboxy ($C_1$-$C_8$) alkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$) alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkyl-carboxamido, an unsubstituted ($C_1$-$C_{18}$ alkyl)aminoalkyl, a substituted or unsubstituted C-carboxy($C_1$-$C_{18}$) alkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy.

In some embodiments, $R_3$, $R_7$, $R_{12}$, and $R_{18}$ are independently selected from the group consisting of hydrogen, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted arylamino-($C_1$-$C_{18}$) alkyl, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted ($C_1$-$C_{18}$ alkyl) aminoalkyl, a substituted or unsubstituted C-carboxy($C_1$-$C_{18}$) alkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy; and $R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and unsubstituted ($C_1$-$C_6$) alkyl.

In some embodiments, $R_3$, $R_7$, $R_{12}$, and $R_{18}$ are independently selected from the group consisting of hydrogen, an unsubstituted ($C_1$-$C_6$) alkyl, unsubstituted ($C_1$-$C_6$) hydroxyalkyl, unsubstituted ($C_1$-$C_{16}$) alkyloxy-($C_1$-$C_5$) alkyl, unsubstituted ($C_1$-$C_{16}$) alkylcarboxy-($C_1$-$C_5$) alkyl, unsubstituted ($C_1$-$C_{16}$) alkylamino-($C_1$-$C_5$)alkyl, ($C_1$-$C_{16}$) alkylamino-($C_1$-$C_5$) alkylamino, unsubstituted ($C_1$-$C_{16}$) alkylamino-($C_1$-$C_{16}$) alkylamino-($C_1$-$C_5$) alkylamino, an unsubstituted ($C_1$-$C_{16}$) aminoalkyl, an unsubstituted arylamino-($C_1$-$C_5$) alkyl, an unsubstituted ($C_1$-$C_5$) aminoalkyloxy, an unsubstituted ($C_1$-$C_{16}$) aminoalkyloxy-($C_1$-$C_5$) alkyl, an unsubstituted ($C_1$-$C_5$) aminoalkylcarboxy, an unsubstituted ($C_1$-$C_5$) aminoalkylaminocarbonyl, an unsubstituted ($C_1$-$C_5$) aminoalkylcarboxamido, an unsubstituted di($C_1$-$C_5$ alkyl)amino-($C_1$-$C_5$) alkyl, a substituted or unsubstituted C-carboxy($C_1$-$C_5$)alkyl, unsubstituted ($C_1$-$C_5$) guanidinoalkyloxy, unsubstituted ($C_1$-$C_{16}$) quaternary ammonium alkylcarboxy, and unsubstituted ($C_1$-$C_{16}$) guanidinoalkylcarboxy;

In some embodiments, $R_1$, $R_2$, $R_4$, $R_5$, $R_6$, $R_8$, $R_{10}$, $R_{11}$, $R_{14}$, $R_{16}$, and $R_{17}$ are each hydrogen; and $R_9$ and $R_{13}$ are each methyl.

In some embodiments, $R_3$, $R_7$, $R_{12}$, and $R_{18}$ are independently selected from the group consisting of aminoalkyloxy; aminoalkylcarboxy; alkylaminoalkyl; alkoxycarbonylalkyl; alkylcarbonylalkyl; di(alkyl)aminoalkyl; C-carboxyalkyl; alkoxycarbonylalkyl; and alkylcarboxyalkyl.

In some embodiments, $R_3$, $R_7$, and $R_{12}$ are independently selected from the group consisting of aminoalkyloxy and aminoalkylcarboxy; and $R_{18}$ is selected from the group consisting of alkylaminoalkyl; alkoxycarbonylalkyl; alkylcarbonyloxyalkyl; di(alkyl)aminoalkyl; C-carboxyalkyl; alkylaminoalkyl; alkyoxycarbonylalkyl; and alkylcarboxyalkyl.

In some embodiments, $R_3$, $R_7$, and $R_{12}$ are the same. In some embodiments, $R_3$, $R_7$, and $R_{12}$ are aminoalkyloxy. In some embodiments, $R_3$, $R_7$, and $R_{12}$ are aminoalkylcarboxy.

In some embodiments, $R_{18}$ is alkylaminoalkyl. In some embodiments, alkoxycarbonylalkyl. In some embodiments, $R_{18}$ is di(alkyl)aminoalkyl. In some embodiments, $R_{18}$ is alkylcarboxyalkyl. In some embodiments, $R_{18}$ is C-carboxyalkyl.

In some embodiments, $R_3$, $R_7$, $R_{12}$, and $R_{18}$ are independently selected from the group consisting of amino-$C_3$-alkyloxy; amino-$C_3$-alkyl-carboxy; $C_8$-alkylamino-$C_5$-alkyl; $C_8$-alkoxy-carbonyl-$C_4$-alkyl; $C_8$-alkyl-carbonyl-$C_4$-alkyl; di-($C_5$-alkyl)amino-$C_5$-alkyl; C-carboxy-$C_4$-alkyl; $C_{13}$-alkylamino-$C_5$-alkyl; $C_6$-alkoxy-carbonyl-$C_4$-alkyl; and $C_6$-alkyl-carboxy-$C_4$-alkyl.

In some embodiments, the CSA, or a pharmaceutically acceptable salt thereof, is:

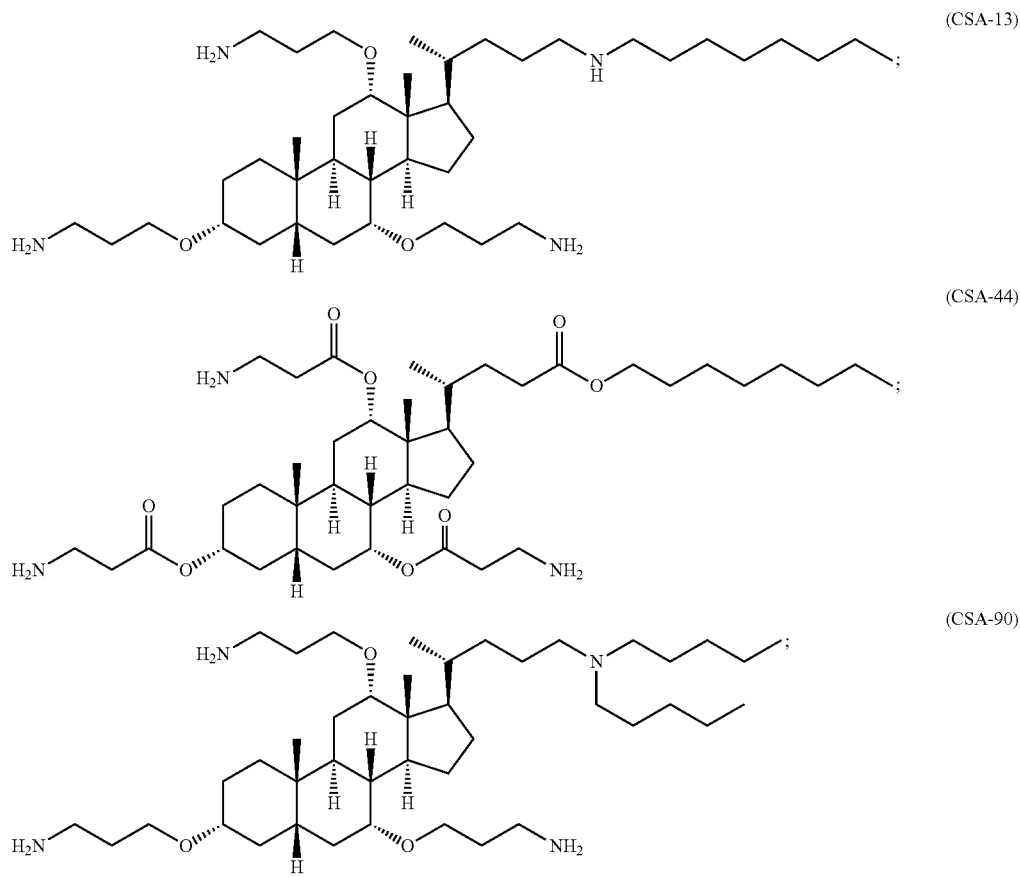

-continued
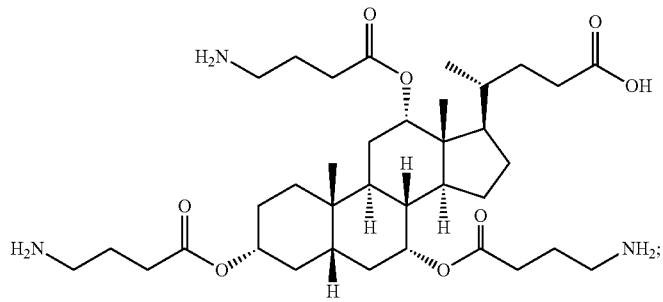
(CSA-56)
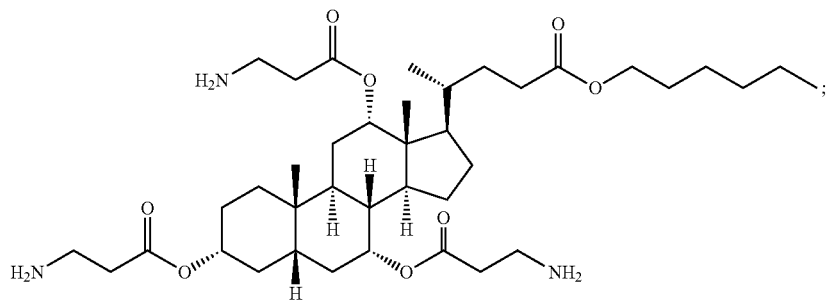
(CSA-142)
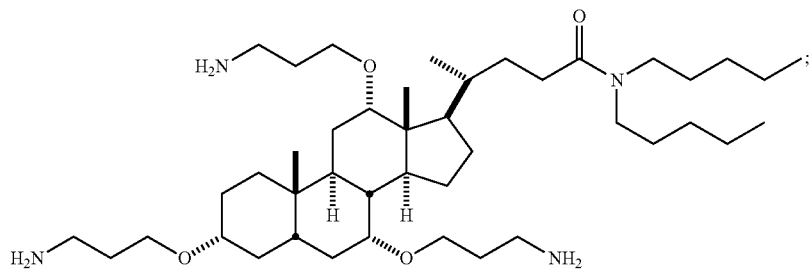
(CSA-190)
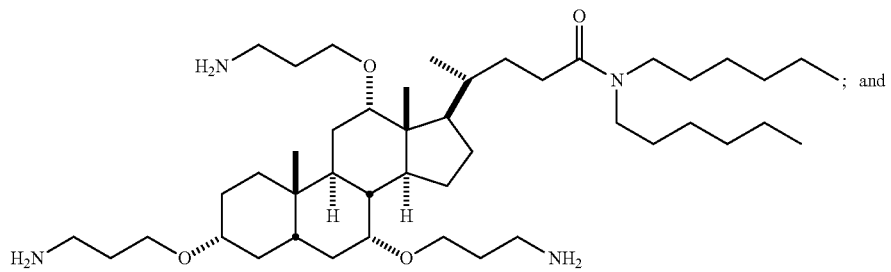
(CSA-191)
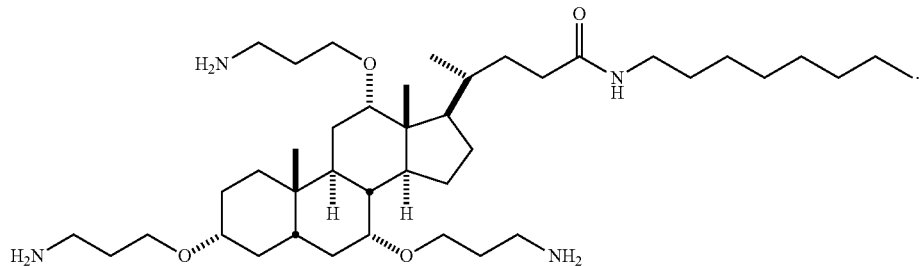
(CSA-192)

In some embodiments, the CSA, or a pharmaceutically acceptable salt thereof, is

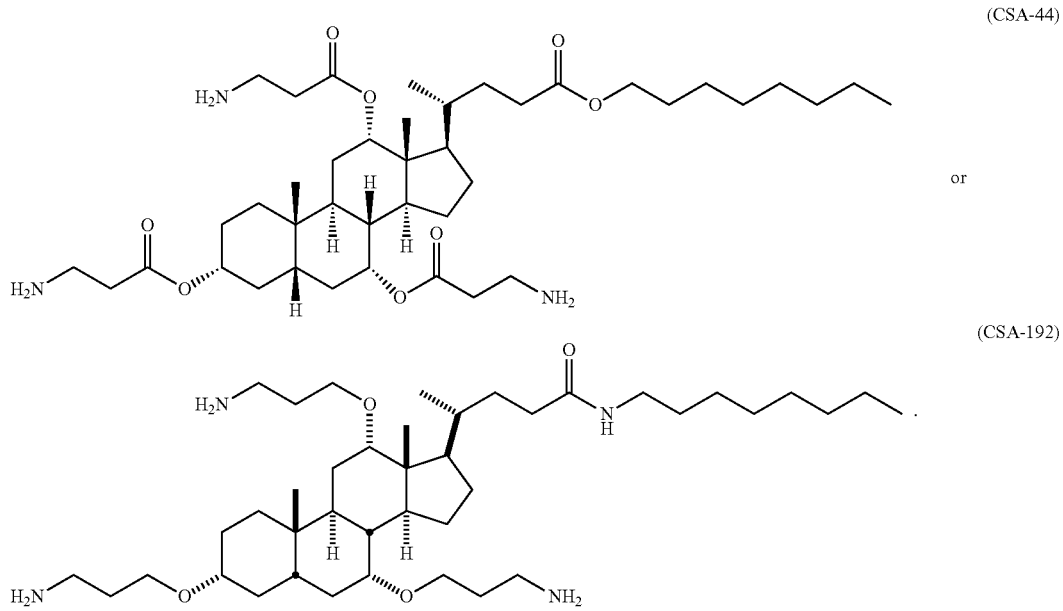

In some embodiments, the pharmaceutically acceptable salt is a hydrochloride salt. In some embodiments, the pharmaceutically acceptable salt is a tri-hydrochloride salt.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

DETAILED DESCRIPTION

The embodiments disclosed herein will now be described by reference to some more detailed embodiments, with occasional reference to the accompanying drawings. These embodiments may, however, be embodied in different forms and should not be construed as limited to the embodiments set forth herein. Rather, these embodiments are provided so that this disclosure will be thorough and complete, and will fully convey the scope of the embodiments to those skilled in the art.

DEFINITIONS

Unless otherwise defined, all technical and scientific terms used herein have the same meaning as commonly understood by one of ordinary skill in the art to which these embodiments belong. The terminology used in the description herein is for describing particular embodiments only and is not intended to be limiting of the embodiments. As used in the specification and the appended claims, the singular forms "a," "an," and "the" are intended to include the plural forms as well, unless the context clearly indicates otherwise. All publications, patent applications, patents, and other references mentioned herein are incorporated by reference in their entirety.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present embodiments. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the embodiments are approximations, the numerical values set forth in the specific examples are reported as precisely as possible. Any numerical value, however, inherently contains certain errors necessarily resulting from the standard deviation found in their respective testing measurements. Every numerical range given throughout this specification and claims will include every narrower numerical range that falls within such broader numerical range, as if such narrower numerical ranges were all expressly written herein. Where a range of values is provided, it is understood that the upper and lower limit, and each intervening value between the upper and lower limit of the range is encompassed within the embodiments.

As used herein, any "R" group(s) such as, without limitation, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ represent substituents that can be attached to the indicated atom. Unless otherwise specified, an R group may be substituted or unsubstituted.

A "ring" as used herein can be heterocyclic or carbocyclic. The term "saturated" used herein refers to a ring having each atom in the ring either hydrogenated or substituted such that the valency of each atom is filled. The term "unsaturated" used herein refers to a ring where the valency of each atom of the ring may not be filled with hydrogen or other substituents. For example, adjacent carbon atoms in the fused ring can be doubly bound to each other. Unsaturation can also include deleting at least one of the following pairs and completing the valency of the ring carbon atoms at these deleted positions with a double bond; such as $R_5$ and $R_9$ $R_8$ and $R_{10}$; and $R_{13}$ and $R_{14}$.

Whenever a group is described as being "substituted" that group may be substituted with one, two, three or more of the indicated substituents, which may be the same or different, each replacing a hydrogen atom. If no substituents are indicated, it is meant that the indicated "substituted" group may be substituted with one or more group(s) individually and independently selected from alkyl, alkenyl, alkynyl, cycloalkyl, cycloalkenyl, cycloalkynyl, acylalkyl, alkoxyalkyl, aminoalkyl, amino acid, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen (e.g., F, Cl, Br, and I), thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, oxo, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, $R_aO(CH_2)_mO—$, $R_b(CH_2)_nO—$, $R_cC(O)O(CH_2)_pO—$, and protected derivatives thereof. The substituent may be attached to the group at more than one attachment point. For example, an aryl group may be substituted with a heteroaryl group at two attachment points to form a fused multicyclic aromatic ring system. Biphenyl and naphthalene are two examples of an aryl group that is substituted with a second aryl group.

As used herein, "$C_a$" or "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3—$, $CH_3CH_2—$, $CH_3CH_2CH_2—$, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 25 carbon atoms (whenever it appears herein, a numerical range such as "1 to 25" refers to each integer in the given range; e.g., "1 to 25 carbon atoms" means that the alkyl group may consist of 1 carbon atom, 2 carbon atoms, 3 carbon atoms, etc., up to and including 25 carbon atoms, although the present definition also covers the occurrence of the term "alkyl" where no numerical range is designated). The alkyl group may also be a medium size alkyl having 1 to 15 carbon atoms. The alkyl group could also be a lower alkyl having 1 to 6 carbon atoms. The alkyl group of the compounds may be designated as "$C_4$" or "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The alkenyl group may have 2 to 25 carbon atoms (whenever it appears herein, a numerical range such as "2 to 25" refers to each integer in the given range; e.g., "2 to 25 carbon atoms" means that the alkenyl group may consist of 2 carbon atom, 3 carbon atoms, 4 carbon atoms, etc., up to and including 25 carbon atoms, although the present definition also covers the occurrence of the term "alkenyl" where no numerical range is designated). The alkenyl group may also be a medium size alkenyl having 2 to 15 carbon atoms. The alkenyl group could also be a lower alkenyl having 1 to 6 carbon atoms. The alkenyl group of the compounds may be designated as "$C_4$" or "$C_2$-$C_4$ alkyl" or similar designations. An alkenyl group may be unsubstituted or substituted.

As used herein, "alkynyl" refers to an alkyl group that contains in the straight or branched hydrocarbon chain one or more triple bonds. The alkynyl group may have 2 to 25 carbon atoms (whenever it appears herein, a numerical range such as "2 to 25" refers to each integer in the given range; e.g., "2 to 25 carbon atoms" means that the alkynyl group may consist of 2 carbon atom, 3 carbon atoms, 4 carbon atoms, etc., up to and including 25 carbon atoms, although the present definition also covers the occurrence of the term "alkynyl" where no numerical range is designated). The alkynyl group may also be a medium size alkynyl having 2 to 15 carbon atoms. The alkynyl group could also be a lower alkynyl having 2 to 6 carbon atoms. The alkynyl group of the compounds may be designated as "$C_4$" or "$C_2$-$C_4$ alkyl" or similar designations. An alkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group (although the definition of $C_6$-$C_{10}$ aryl covers the occurrence of "aryl" when no numerical range is designated). Examples of aryl groups include, but are not limited to, benzene, naphthalene and azulene. An aryl group may be substituted or unsubstituted.

As used herein, "aralkyl" and "aryl(alkyl)" refer to an aryl group connected, as a substituent, via a lower alkylene group. The aralkyl group may have 6 to 20 carbon atoms (whenever it appears herein, a numerical range such as "6 to 20" refers to each integer in the given range; e.g., "6 to 20 carbon atoms" means that the aralkyl group may consist of 6 carbon atom, 7 carbon atoms, 8 carbon atoms, etc., up to and including 20 carbon atoms, although the present definition also covers the occurrence of the term "aralkyl" where no numerical range is designated). The lower alkylene and aryl group of an aralkyl may be substituted or unsubstituted. Examples include but are not limited to benzyl, 2-phenylalkyl, 3-phenylalkyl, and naphthylalkyl.

"Lower alkylene groups" refer to a $C_1$-$C_{25}$ straight-chained alkyl tethering groups, such as —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "alkoxy" or "alkyloxy" refers to the formula —OR wherein R is an alkyl, an alkenyl, an alkynyl, a cycloalkyl, a cycloalkenyl or a cycloalkynyl as defined above. A non-limiting list of alkoxys are methoxy, ethoxy, n-propoxy, 1-methylethoxy (isopropoxy), n-butoxy, iso-butoxy, sec-butoxy and tert-butoxy. An alkoxy may be substituted or unsubstituted.

As used herein, "acyl" refers to a hydrogen, alkyl, alkenyl, alkynyl, aryl, or heteroaryl connected, as substituents, via a carbonyl group. Examples include formyl, acetyl, propanoyl, benzoyl, and acryl. An acyl may be substituted or unsubstituted.

As used herein, "alkoxyalkyl" or "alkyloxyalkyl" refers to an alkoxy group connected, as a substituent, via a lower alkylene group. Examples include alkyl-O-alkyl- and alkoxy-alkyl- with the terms alkyl and alkoxy defined herein.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

The term "amino" as used herein refers to a —NH$_2$ group.

As used herein, the term "hydroxy" refers to a —OH group.

A "cyano" group refers to a "—CN" group.

A "carbonyl" or an "oxo" group refers to a C=O group.

The term "azido" as used herein refers to a —N$_3$ group.

As used herein, "aminoalkyl" refers to an amino group connected, as a substituent, via a lower alkylene group. Examples include H$_2$N-alkyl- with the term alkyl defined herein.

As used herein, "alkylcarboxyalkyl" refers to an alkyl group connected, as a substituent, to a carboxy group that is connected, as a substituent, to an alkyl group. Examples include alkyl-C(=O)O-alkyl- and alkyl-O—C(=O)-alkyl- with the term alkyl as defined herein.

As used herein, "C-carboxyalkyl" refers to a carboxy group connected, as a substituent, to an alkyl group. Examples include HO—(C=O)-alkyl, with the term alkyl as defined herein.

As used herein, "alkylaminoalkyl" refers to an alkyl group connected, as a substituent, to an amino group that is connected, as a substituent, to an alkyl group. Examples include alkyl-NH-alkyl-, with the term alkyl as defined herein.

As used herein, "dialkylaminoalkyl" or "di(alkyl)amino-alkyl" refers to two alkyl groups connected, each as a substituent, to an amino group that is connected, as a substituent, to an alkyl group. Examples include

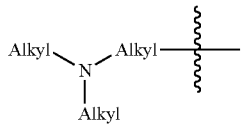

with the term alkyl as defined herein.

As used herein, "alkylaminoalkylamino" refers to an alkyl group connected, as a substituent, to an amino group that is connected, as a substituent, to an alkyl group that is connected, as a substituent, to an amino group. Examples include alkyl-NH-alkyl-NH—, with the term alkyl as defined herein.

As used herein, "alkylaminoalkylaminoalkylamino" refers to an alkyl group connected, as a substituent, to an amino group that is connected, as a substituent, to an alkyl group that is connected, as a substituent, to an amino group that is connected, as a substituent, to an alkyl group. Examples include alkyl-NH-alkyl-NH-alkyl-, with the term alkyl as defined herein.

As used herein, "arylaminoalkyl" refers to an aryl group connected, as a substituent, to an amino group that is connected, as a substituent, to an alkyl group. Examples include aryl-NH-alkyl-, with the terms aryl and alkyl as defined herein.

As used herein, "aminoalkyloxy" refers to an amino group connected, as a substituent, to an alkyloxy group. Examples include H$_2$N-alkyl-O— and H$_2$N-alkoxy- with the terms alkyl and alkoxy as defined herein.

As used herein, "aminoalkyloxyalkyl" refers to an amino group connected, as a substituent, to an alkyloxy group connected, as a substituent, to an alkyl group. Examples include H$_2$N-alkyl-O-alkyl- and H$_2$N-alkoxy-alkyl- with the terms alkyl and alkoxy as defined herein.

As used herein, "aminoalkylcarboxy" refers to an amino group connected, as a substituent, to an alkyl group connected, as a substituent, to a carboxy group. Examples include H$_2$N-alkyl-C(=O)O— and H$_2$N-alkyl-O—C(=O)— with the term alkyl as defined herein.

As used herein, "aminoalkylaminocarbonyl" refers to an amino group connected, as a substituent, to an alkyl group connected, as a substituent, to an amino group connected, as a substituent, to a carbonyl group. Examples include H$_2$N-alkyl-NH—C(=O)— with the term alkyl as defined herein.

As used herein, "aminoalkylcarboxamido" refers to an amino group connected, as a substituent, to an alkyl group connected, as a substituent, to a carbonyl group connected, as a substituent to an amino group. Examples include H$_2$N-alkyl-C(=O)—NH— with the term alkyl as defined herein.

As used herein, "azidoalkyloxy" refers to an azido group connected as a substituent, to an alkyloxy group. Examples include N$_3$-alkyl-O— and N$_3$-alkoxy- with the terms alkyl and alkoxy as defined herein.

As used herein, "cyanoalkyloxy" refers to a cyano group connected as a substituent, to an alkyloxy group. Examples include NC-alkyl-O— and NC-alkoxy- with the terms alkyl and alkoxy as defined herein.

As used herein, "guanidinoalkyloxy" refers to a guanidinyl group connected, as a substituent, to an alkyloxy group. Examples include

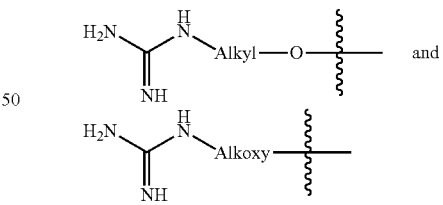

with the terms alkyl and alkoxy as defined herein.

As used herein, "guanidinoalkylcarboxy" refers to a guanidinyl group connected, as a substituent, to an alkyl group connected, as a substituent, to a carboxy group. Examples include

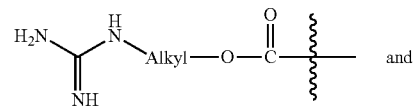

-continued

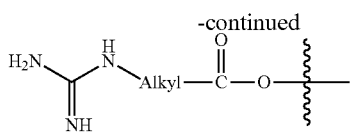

with the term alkyl as defined herein.

As used herein, "quaternary ammonium alkylcarboxy" refers to a quaternized amino group connected, as a substituent, to an alkyl group connected, as a substituent, to a carboxy group. Examples include

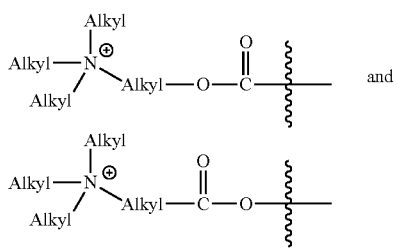

with the term alkyl as defined herein.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens.

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine.

A linking group is a divalent moiety used to link one steroid to another steroid. In some embodiments, the linking group is used to link a first CSA with a second CSA (which may be the same or different). An example of a linking group is ($C_1$-$C_{10}$) alkyloxy-($C_1$-$C_{10}$) alkyl.

The terms "P.G." or "protecting group" or "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein). Amino-protecting groups are known to those skilled in the art. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the disclosure.

CSA Compounds

Compounds useful in accordance with this disclosure are described herein, both generically and with particularity, and in U.S. Pat. Nos. 6,350,738, 6,486,148, 6,767,904, 7,598,234, 7,754,705, and 8,975,310, which are incorporated herein by reference. Compounds include steroid derivatives, such as cationic steroid antimicrobials ("CSAs") that exhibit one or more wound healing activities or functions.

CSA compounds, are synthetically produced small molecules that include a sterol backbone having various charged groups (e.g., amine and cationic groups) attached to the backbone. The backbone can be used to orient the amine or guanidine groups on one face, or plane, of the sterol backbone.

CSAs are cationic and amphiphilic, based upon the functional groups attached to the backbone. They are facially amphiphilic with a hydrophobic face and a polycationic face. For example, a scheme showing a compound having primary amino groups on one face, or plane, of a backbone is shown below in Scheme I:

Scheme I

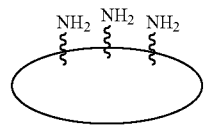

The charged groups are believed to be responsible for antimicrobial properties. For example, the charged groups may disrupt the bacterial cellular membrane to cause cell death or sensitization.

In some embodiments the CSA compound may have a formula as set forth in Formula (V) or a pharmaceutically acceptable salt thereof:

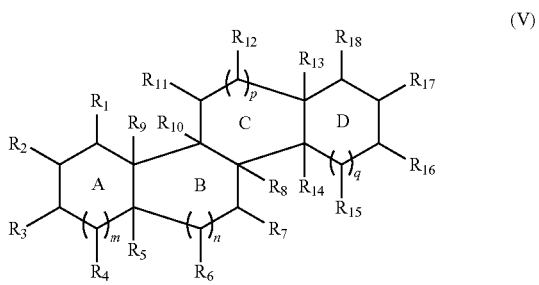

(V)

Where m, n, p, and q are independently 0 or 1; $R_1$-$R_{18}$ represent substituents that are attached to the indicated atom on the steroid backbone (i.e., steroid group); and at least two, preferably at least three, of $R_1$-$R_{18}$ each include a cationic group.

In one embodiment, rings A, B, C, and D are independently saturated, or are fully or partially unsaturated, provided that at least two of rings A, B, C, and D are saturated; m, n, p, and q are independently 0 or 1; $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted alkyl, substituted or unsubstituted hydroxyalkyl, substituted or unsubstituted alkyloxyalkyl, substituted or unsubstituted alkylcarboxyalkyl, substituted or unsubstituted alkylaminoalkyl, substituted or unsubstituted alkylaminoalkylamino, substituted or unsubstituted alkylaminoalkylaminoalkylamino, a substituted or unsubstituted aminoalkyl, a substituted or unsubstituted aryl, a substituted or unsubstituted arylaminoalkyl, substituted or unsubstituted haloalkyl, substituted or unsubstituted alkenyl, substituted or unsubstituted alkynyl, oxo, a linking group attached to a second steroid, a substituted or unsubstituted aminoalkyloxy, a substituted or unsubstituted aminoalkyloxyalkyl, a substituted or unsubstituted aminoalkylcarboxy, a substituted or unsubstituted aminoalkylaminocarbonyl, a substituted or unsubstituted aminoalkylcarboxamido, a substituted or unsubstituted di(alkyl)aminoalkyl, a substituted or unsubstituted C-carboxyalkyl, $H_2N$—$HC(Q_5)$-$C(O)$—O—, $H_2N$—$HC(Q_5)$-$C(O)$—$N(H)$—, substituted or unsubstituted azidoalkyloxy, substituted or unsubstituted cyanoalkyloxy, P.G.-HN—$HC(Q_5)$-$C(O)$—O—, substituted or unsubstituted guanidinoalkyloxy, substituted or unsubstituted quaternary ammonium alkylcarboxy, and substituted or unsubstituted guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted alkyl, substituted or unsubstituted hydroxyalkyl, substituted or unsubstituted alkyloxyalkyl, a substituted or unsubstituted aminoalkyl, a substituted or unsubstituted aryl, substituted or unsubstituted haloalkyl, substituted or unsubstituted alkenyl, substituted or unsubstituted alkynyl, oxo, a linking group attached to a second steroid, a substituted or unsubstituted aminoalkyloxy, a substituted or unsubstituted aminoalkylcarboxy, a substituted or unsubstituted aminoalkylaminocarbonyl, a substituted or unsubstituted di(alkyl)aminoalkyl, a substituted or unsubstituted C-carboxyalkyl, $H_2NHC(Q_5)$-$C(O)$—O—, $H_2N$—$HC(Q_5)$-$C(O)$—$N(H)$—, substituted or unsubstituted azidoalkyloxy, substituted or unsubstituted cyanoalkyloxy, P.G.-HN—$HC(Q_5)$-$C(O)$—O—, substituted or unsubstituted guanidinoalkyloxy, and substituted or unsubstituted guanidinoalkylcarboxy, where $Q_5$ is a side chain of any amino acid, P.G. is an amino protecting group; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted aminoalkyl, a substituted or unsubstituted aminoalkyloxy, substituted or unsubstituted alkylcarboxyalkyl, substituted or unsubstituted alkylaminoalkylamino, substituted or unsubstituted alkylaminoalkylaminoalkylamino, a substituted or unsubstituted aminoalkylcarboxy, a substituted or unsubstituted arylaminoalkyl, a substituted or unsubstituted aminoalkyloxyaminoalkylaminocarbonyl, a substituted or unsubstituted aminoalkylaminocarbonyl, a substituted or unsubstituted aminoalkylcarboxamido, a substituted or unsubstituted quaternary ammonium alkylcarboxy, a substituted or unsubstituted di(alkyl)aminoalkyl, a substituted or unsubstituted C-carboxyalkyl, $H_2N$—$HC(Q_5)$-$C(O)$—O—, $H_2N$—$HC(Q_5)$-$C(O)$—$N(H)$—, substituted or unsubstituted azidoalkyloxy, substituted or unsubstituted cyanoalkyloxy, P.G.-HN—$HC(Q_5)$-$C(O)$—O—, substituted or unsubstituted guanidinoalkyloxy, and a substituted or unsubstituted guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted ($C_1$-$C_{18}$) alkyl, substituted or unsubstituted ($C_1$-$C_{18}$) hydroxyalkyl, substituted or unsubstituted ($C_1$-$C_{18}$) alkyloxy-($C_1$-$C_{18}$) alkyl, substituted or unsubstituted ($C_1$-$C_{18}$) alkylcarboxy-($C_1$-$C_{18}$) alkyl, substituted or unsubstituted ($C_1$-$C_{18}$) alkylamino-($C_1$-$C_{18}$)alkyl, substituted or unsubstituted ($C_1$-$C_{18}$) alkylamino-($C_1$-$C_{18}$) alkylamino, substituted or unsubstituted ($C_1$-$C_{18}$) alkylamino-($C_1$-$C_{18}$) alkylamino-($C_1$-$C_{18}$) alkylamino, a substituted or unsubstituted ($C_1$-$C_{18}$) aminoalkyl, a substituted or unsubstituted aryl, a substituted or unsubstituted arylamino-($C_1$-$C_{18}$) alkyl, substituted or unsubstituted ($C_1$-$C_{18}$) haloalkyl, substituted or unsubstituted ($C_2$-$C_6$) alkenyl, substituted or unsubstituted ($C_2$-$C_6$) alkynyl, oxo, a linking group attached to a second steroid, a substituted or unsubstituted ($C_1$-$C_{18}$) aminoalkyloxy, a substituted or unsubstituted ($C_1$-$C_{18}$) aminoalkyloxy-($C_1$-$C_{18}$) alkyl, a substituted or unsubstituted ($C_1$-$C_{18}$) aminoalkylcarboxy, a substituted or unsubstituted ($C_1$-$C_{18}$) aminoalkylaminocarbonyl, a substituted or unsubstituted ($C_1$-$C_{18}$) aminoalkylcarboxamido, a substituted or unsubstituted di($C_1$-$C_{18}$ alkyl)aminoalkyl, a substituted or unsubstituted C-carboxy($C_1$-$C_{18}$)alkyl, $H_2N$—$HC(Q_5)$-$C(O)$—O—, $H_2N$—$HC(Q_5)$-$C(O)$—$N(H)$—, substituted or unsubstituted ($C_1$-$C_{18}$) azidoalkyloxy, substituted or unsubstituted ($C_1$-$C_{18}$) cyanoalkyloxy, P.G.-HN—$HC(Q_5)$-$C(O)$—O—, substituted or unsubstituted ($C_1$-$C_{18}$) guanidinoalkyloxy, substituted or unsubstituted ($C_1$-$C_{18}$) quaternary ammonium alkylcarboxy, and substituted or unsubstituted ($C_1$-$C_{18}$) guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted ($C_1$-$C_{18}$) alkyl, substituted or unsubstituted ($C_1$-$C_{18}$) hydroxyalkyl, substituted or unsubstituted ($C_1$-$C_{18}$) alkyloxy-($C_1$-$C_{18}$) alkyl, a substituted or unsubstituted ($C_1$-$C_{18}$) aminoalkyl, a substituted or unsubstituted aryl, substituted or unsubstituted ($C_1$-$C_{18}$) haloalkyl, substituted or unsubstituted ($C_2$-$C_6$) alkenyl, substituted or unsubstituted ($C_2$-$C_6$) alkynyl, oxo, a linking group attached to a second steroid, a substituted or unsubstituted ($C_1$-$C_{18}$) aminoalkyloxy, a substituted or unsubstituted ($C_1$-$C_{18}$) aminoalkylcarboxy, a substituted or unsubstituted ($C_1$-$C_{18}$) aminoalkylaminocarbonyl, di($C_1$-$C_{18}$ alkyl)aminoalkyl, a substituted or unsubstituted C-carboxy($C_1$-$C_{18}$)alkyl, $H_2N$—HC($Q_5$)-C(O)—O—, $H_2N$—HC($Q_5$)-C(O)—N(H)—, substituted or unsubstituted ($C_1$-$C_{18}$) azidoalkyloxy, substituted or unsubstituted ($C_1$-$C_{18}$) cyanoalkyloxy, P.G.-HN—HC($Q_5$)-C(O)—O—, substituted or unsubstituted ($C_1$-$C_{18}$) guanidinoalkyloxy, and substituted or unsubstituted ($C_1$-$C_{18}$) guanidinoalkylcarboxy, where $Q_5$ is a side chain of any amino acid, and P.G. is an amino protecting group; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted ($C_1$-$C_{18}$) aminoalkyl, a substituted or unsubstituted ($C_1$-$C_{18}$) aminoalkyloxy, substituted or unsubstituted ($C_1$-$C_{18}$) alkylcarboxy-($C_1$-$C_{18}$) alkyl, substituted or unsubstituted ($C_1$-$C_{18}$) alkylamino-($C_1$-$C_{18}$) alkylamino, substituted or unsubstituted ($C_1$-$C_{18}$) alkylamino-($C_1$-$C_{18}$) alkylamino ($C_1$-$C_{18}$) alkylamino, a substituted or unsubstituted ($C_1$-$C_{18}$) aminoalkylcarboxy, a substituted or unsubstituted arylamino ($C_1$-$C_{18}$) alkyl, a substituted or unsubstituted ($C_1$-$C_{18}$) aminoalkyloxy ($C_1$-$C_{18}$) aminoalkylaminocarbonyl, a substituted or unsubstituted ($C_1$-$C_{18}$) aminoalkylaminocarbonyl, a substituted or unsubstituted ($C_1$-$C_{18}$) aminoalkylcarboxyamido, a substituted or unsubstituted ($C_1$-$C_{18}$) quaternary ammonium alkylcarboxy, substituted or unsubstituted di($C_1$-$C_{18}$ alkyl)aminoalkyl, a substituted or unsubstituted C-carboxy($C_1$-$C_{18}$)alkyl, $H_2N$—HC($Q_5$)-C(O)—O—, $H_2N$—HC($Q_5$)-C(O)—N(H)—, substituted or unsubstituted ($C_1$-$C_{18}$) azidoalkyloxy, substituted or unsubstituted ($C_1$-$C_{18}$) cyanoalkyloxy, P.G.-HN—HC($Q_5$)-C(O)—O—, substituted or unsubstituted ($C_1$-$C_{18}$) guanidinoalkyloxy, and a substituted or unsubstituted ($C_1$-$C_{18}$) guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, an unsubstituted C-carboxy($C_1$-$C_{18}$)alkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$) alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, an unsubstituted C-carboxy($C_1$-$C_{18}$)alkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy.

In some embodiments, the compounds or pharmaceutically acceptable salts thereof of Formula (V) can be also represented by Formula (I):

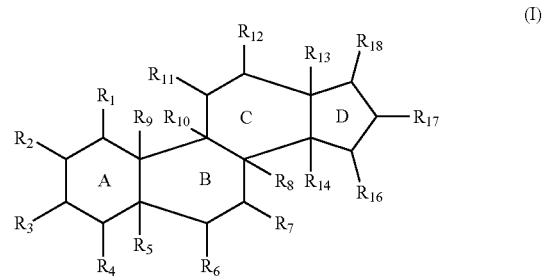

(I)

wherein fused rings A, B, C, and D are independently saturated or fully or partially unsaturated; and each of $R_1$ through $R_4$, $R_6$, $R_7$, $R_{11}$, $R_{12}$, $R_{16}$, $R_{17}$, and $R_{18}$ is independently selected from the group consisting of hydrogen, hydroxyl, a substituted or unsubstituted ($C_1$-$C_{10}$) alkyl, ($C_1$-$C_{10}$) hydroxyalkyl, ($C_1$-$C_{10}$) alkyloxy-($C_1$-$C_{10}$) alkyl, ($C_1$-$C_{10}$) alkylcarboxy-($C_1$-$C_{10}$) alkyl, $C_1$-$C_{10}$) alkylamino-($C_1$-$C_{10}$) alkyl, ($C_1$-$C_{10}$) alkylamino-($C_1$-$C_{10}$) alkylamino, ($C_1$-$C_{10}$) alkylamino-($C_1$-$C_{10}$) alkylamino-($C_1$-$C_{10}$) alkylamino, a substituted or unsubstituted ($C_1$-$C_{10}$) aminoalkyl, a substituted or unsubstituted aryl, a substituted or unsubstituted arylamino-($C_1$-$C_{10}$) alkyl, ($C_1$-$C_{10}$) haloalkyl, $C_2$-$C_6$ alkenyl, $C_2$-$C_6$ alkynyl, oxo, a linking group attached to a second steroid, a substituted or unsubstituted ($C_1$-$C_{10}$) aminoalkyloxy, a substituted or unsubstituted ($C_1$-$C_{10}$) aminoalkyloxy-($C_1$-$C_{10}$) alkyl, a substituted or unsubstituted ($C_1$-$C_{10}$) aminoalkylcarboxy, a substituted or unsubstituted ($C_1$-$C_{10}$) aminoalkylaminocarbonyl, a substituted or unsubstituted ($C_1$-$C_{10}$) aminoalkylcarboxamido, a substituted or unsubstituted C-carboxy($C_1$-$C_{10}$)alkyl, $H_2N$—HC($Q_5$)-C(O)—O—, $H_2N$—HC($Q_5$)-C(O)—N(H)—, ($C_1$-$C_{10}$) azidoalkyloxy, ($C_1$-$C_{10}$) cyanoalkyloxy, P.G.-HN—HC($Q_5$)-C(O)—O—, ($C_1$-$C_{10}$) guanidinoalkyloxy, ($C_1$-$C_{10}$) quaternary ammonium alkylcarboxy, and ($C_1$-$C_{10}$) guanidinoalkyl carboxy, where $Q_5$ is a side chain of any amino acid (including the side chain of glycine, i.e., H), PG. is an amino protecting group, and $R_5$, $R_8$, $R_9$, $R_{10}$, $R_{13}$, and $R_{14}$ is each independently: deleted when one of fused rings A, B, C, or D is unsaturated so as to complete the valency of the carbon atom at that site, or selected from the group consisting of hydrogen, hydroxyl, 10 a substituted or unsubstituted ($C_1$-$C_{10}$) alkyl, ($C_1$-$C_{10}$) hydroxyalkyl, ($C_1$-$C_{10}$) alkyloxy-($C_1$-$C_{10}$) alkyl, a substituted or unsubstituted ($C_1$-$C_{10}$) aminoalkyl, a substituted or unsubstituted aryl, $C_1$-$C_{10}$ haloalkyl, $C_2$-$C_6$ alkenyl, $C_2$-$C_6$ alkynyl, oxo, a linking group attached to a second steroid, a substituted or unsubstituted ($C_1$-$C_{10}$) aminoalkyloxy, a substituted or unsubstituted ($C_1$-$C_{10}$) aminoalkylcarboxy, a substituted or unsubstituted ($C_1$-$C_{10}$) aminoalkylaminocarbonyl, $H_2N$—HC($Q_5$)-C(O)—O—, $H_2N$—HC($Q_5$)-C(O)—N(H)—, ($C_1$-$C_{10}$) azidoalkyloxy, ($C_1$-$C_{10}$) cyanoalkyloxy, P.G.-HN—HC($Q_5$)-C(O)—O—, ($C_1$-$C_{10}$) guanidinoalkyloxy, and ($C_1$-$C_{10}$) guanidinoalkylcarboxy, where $Q_5$ is a side chain of any amino acid, PG. is an amino protecting group, and provided that at least two of $R_1$ through $R_{14}$ are independently selected from the group consisting of a substituted or unsubstituted ($C_1$-$C_{10}$) aminoalkyloxy, ($C_1$-$C_{10}$) alkylcarboxy-($C_1$-$C_{10}$) alkyl, ($C_1$-$C_{10}$) alkylamino-($C_1$-$C_{10}$) alkylamino, ($C_1$-$C_{10}$) alkylamino-($C_1$-$C_{10}$) alkylamino-($C_1$-$C_{10}$) alkylamino, a substituted or unsubstituted ($C_1$-$C_{10}$) aminoalkylcarboxy, a substituted or unsubstituted arylamino($C_1$-$C_{10}$) alkyl, a substituted or unsubstituted ($C_1$-$C_{10}$) aminoalkyloxy-($C_1$-$C_{10}$) alkyl, a substituted or unsubstituted ($C_1$-$C_{10}$) aminoalkylaminocarbonyl, ($C_1$-$C_{10}$) quaternary ammonium alkylcarboxy, $H_2N$—HC($Q_5$)C(O)—O—, $H_2N$—HC($Q_5$)-C(O)—N(H)—, ($C_1$-$C_{10}$) azidoalkyloxy, ($C_1$-$C_{10}$)cyanoalkyloxy, PG.-HN—HC($Q_5$)-C(O)—O—, ($C_1$-$C_{10}$) guanidinoalkyloxy, and ($C_1$-$C_{10}$) guanidinoalkylcarboxy; or a pharmaceutically acceptable salt thereof.

In some embodiments, rings A, B, C, and D are independently saturated, heterocyclic, and/or non-heterocyclic.

In some embodiments, $R_3$, $R_7$, $R_{12}$, and $R_{18}$ are independently selected from the group consisting of hydrogen, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted arylamino-($C_1$-$C_{18}$) alkyl, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl) aminoalkyl, an unsubstituted C-carboxy($C_1$-$C_{18}$)alkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy; and $R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and unsubstituted ($C_1$-$C_6$) alkyl.

In some embodiments, $R_1$, $R_2$, $R_4$, $R_5$, $R_6$, $R_8$, $R_{10}$, $R_{11}$, $R_{14}$, $R_{16}$, and $R_{17}$ are each hydrogen; and $R_9$ and $R_{13}$ are each methyl.

In some embodiments, $R_3$, $R_7$, $R_{12}$, and $R_{18}$ are independently selected from the group consisting of aminoalkyloxy; aminoalkylcarboxy; alkylaminoalkyl; alkoxycarbonylalkyl; alkylcarbonylalkyl; di(alkyl)aminoalkyl; C-carboxyalkyl; alkoxycarbonylalkyl; and alkylcarboxyalkyl.

In some embodiments, $R_3$, $R_7$, and $R_{12}$ are independently selected from the group consisting of aminoalkyloxy and aminoalkylcarboxy; and $R_{18}$ is selected from the group consisting of alkylaminoalkyl; alkoxycarbonylalkyl; alkylcarbonyloxyalkyl; di(alkyl)aminoalkyl; alkylaminoalkyl; alkyoxycarbonylalkyl; and alkylcarboxyalkyl.

In some embodiments, $R_3$, $R_7$, and $R_{12}$ are the same substituent or different substituents and/or may be independently an aminoalkyloxy and/or an aminoalkylcarboxy. In some embodiments, $R_{18}$ is alkylaminoalkyl, alkoxycarbonylalkyl, di(alkyl)aminoalkyl, C-carboxyalkyl, or an alkylcarboxyalkyl. In some embodiments, $R_3$, $R_7$, $R_{12}$, and $R_{18}$ are independently selected from the group consisting of amino-$C_3$-alkyloxy; amino-$C_3$-alkyl-carboxy; $C_8$-alkylamino-$C_5$-alkyl; $C_8$-alkoxy-carbonyl-$C_4$-alkyl; $C_8$-alkylcarbonyl-$C_4$-alkyl; di-($C_5$-alkyl)amino-$C_5$-alkyl; C-carboxy-$C_4$-alkyl; $C_{13}$-alkylamino-$C_5$-alkyl; $C_6$-alkoxycarbonyl-$C_4$-alkyl; and $C_6$-alkyl-carboxy-$C_4$-alkyl.

In some embodiments, the compounds or pharmaceutically acceptable salts thereof of Formula (V) can be also represented by Formula (Ia):

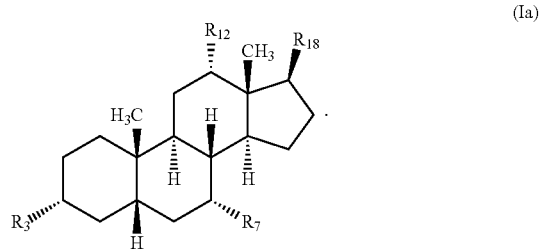

(Ia)

In some embodiments, $R_3$, $R_7$, and $R_{12}$ are independently selected from the group consisting of hydrogen, an unsubstituted ($C_1$-$C_{22}$) alkyl, unsubstituted ($C_1$-$C_{22}$) hydroxyalkyl, unsubstituted ($C_1$-$C_{22}$) alkyloxy-($C_1$-$C_{22}$) alkyl, unsubstituted ($C_1$-$C_{22}$) alkylcarboxy-($C_1$-$C_{22}$) alkyl, unsubstituted ($C_1$-$C_{22}$) alkylamino-($C_1$-$C_{22}$)alkyl, unsubstituted ($C_1$-$C_{22}$) alkylamino-($C_1$-$C_{22}$) alkylamino, unsubstituted ($C_1$-$C_{22}$) alkylamino-($C_1$-$C_{22}$) alkylamino-($C_1$-$C_{18}$) alkylamino, an unsubstituted ($C_1$-$C_{22}$) aminoalkyl, an unsubstituted arylamino-($C_1$-$C_{22}$) alkyl, an unsubstituted ($C_1$-$C_{22}$) aminoalkyloxy, an unsubstituted ($C_1$-$C_{22}$) aminoalkyloxy-($C_1$-$C_{22}$) alkyl, an unsubstituted ($C_1$-$C_{22}$) aminoalkylcarboxy, an unsubstituted ($C_1$-$C_{22}$) aminoalkylaminocarbonyl, an unsubstituted ($C_1$-$C_{22}$) aminoalkylcarboxamido, an unsubstituted di($C_1$-$C_{22}$ alkyl)aminoalkyl, unsubstituted ($C_1$-$C_{22}$) guanidinoalkyloxy, unsubstituted ($C_1$-$C_{22}$) quaternary ammonium alkylcarboxy, and unsubstituted ($C_1$-$C_{22}$) guanidinoalkyl carboxy.

In some embodiments, $R_3$, $R_7$, and $R_{12}$ are independently selected from the group consisting of hydrogen, an unsubstituted ($C_1$-$C_6$) alkyl, unsubstituted ($C_1$-$C_6$) hydroxyalkyl, unsubstituted ($C_1$-$C_{16}$) alkyloxy-($C_1$-$C_5$) alkyl, unsubstituted ($C_1$-$C_{16}$) alkylcarboxy-($C_1$-$C_5$) alkyl, unsubstituted ($C_1$-$C_{16}$) alkylamino-($C_1$-$C_5$)alkyl, unsubstituted ($C_1$-$C_{16}$) alkylamino-($C_1$-$C_5$) alkylamino, unsubstituted ($C_1$-$C_{16}$)

alkylamino-$(C_1$-$C_{16})$ alkylamino-$(C_1$-$C_5)$ alkylamino, an unsubstituted $(C_1$-$C_{16})$ aminoalkyl, an unsubstituted arylamino-$(C_1$-$C_5)$ alkyl, an unsubstituted $(C_1$-$C_5)$ aminoalkyloxy, an unsubstituted $(C_1$-$C_{16})$ aminoalkyloxy-$(C_1$-$C_5)$ alkyl, an unsubstituted $(C_1$-$C_5)$ aminoalkylcarboxy, an unsubstituted $(C_1$-$C_5)$ aminoalkylaminocarbonyl, an unsubstituted $(C_1$-$C_5)$ aminoalkylcarboxamido, an unsubstituted di$(C_1$-$C_5$ alkyl)amino-$(C_1$-$C_5)$ alkyl, unsubstituted $(C_1$-$C_5)$ guanidinoalkyloxy, unsubstituted $(C_1$-$C_{16})$ quaternary ammonium alkylcarboxy, and unsubstituted $(C_1$-$C_{16})$ guanidinoalkylcarboxy.

In some embodiments, $R_3$, $R_7$, and $R_{12}$ are independently selected from the group consisting of aminoalkyloxy; aminoalkylcarboxy; alkylaminoalkyl; alkoxycarbonylalkyl; alkylcarbonylalkyl; di(alkyl)aminoalkyl; alkylcarboxyalkyl; and hydroxyalkyl.

In some embodiments, $R_3$, $R_7$, and $R_{12}$ are independently selected from the group consisting of aminoalkyloxy and aminoalkylcarboxy.

In some embodiments, $R_3$, $R_7$, and $R_{12}$ are the same. In some embodiments, $R_3$, $R_7$, and $R_{12}$ are aminoalkyloxy. In some embodiments, $R_3$, $R_7$, and $R_{12}$ are aminoalkylcarboxy.

In some embodiments, $R_3$, $R_7$, and $R_{12}$ are independently selected from the group consisting of amino-$C_3$-alkyloxy; amino-$C_3$-alkyl-carboxy; $C_8$-alkylamino-$C_5$-alkyl; $C_8$-alkoxy-carbonyl-$C_4$-alkyl; $C_8$-alkyl-carbonyl-$C_4$-alkyl; di-($C_5$-alkyl)amino-$C_5$-alkyl; $C_{13}$-alkylamino-$C_5$-alkyl; $C_6$-alkoxy-carbonyl-$C_4$-alkyl; $C_6$-alkyl-carboxy-$C_4$-alkyl; and $C_{16}$-alkylamino-$C_5$-alkyl.

In some embodiments, CSA compounds as disclosed herein can be a compound of Formula (I), Formula (II), Formula (III), or salts thereof wherein at least $R_{18}$ of the steroidal backbone includes amide functionality in which the carbonyl group of the amide is positioned between the amido nitrogen of the amide and fused ring D of the steroidal backbone. For example, any of the embodiments described above can substitute $R_{18}$ for an $R_{18}$ including amide functionality in which the carbonyl group of the amide is positioned between the amido nitrogen of the amide and fused ring D of the steroidal backbone.

In some embodiments, at least $R_{18}$ can have the following structure:

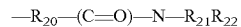

wherein $R_{20}$ is omitted or alkyl, alkenyl, alkynyl, or aryl, and $R_{21}$ and $R_{22}$ are independently selected from the group consisting of hydrogen, alkyl, alkenyl, alkynyl, or aryl, provided that at least one of $R_{21}$ and $R_{22}$ is not hydrogen.

In some embodiments, $R_{21}$ and $R_{22}$ are independently selected from the group consisting of hydrogen, $C_1$-$C_{24}$ alkyl, $C_2$-$C_{24}$ alkenyl, $C_2$-$C_{24}$ alkynyl, $C_6$ or $C_{10}$ aryl, 5 to 10 membered heteroaryl, 5 to 10 membered heterocyclyl, $C_{7-13}$ aralkyl, (5 to 10 membered heteroaryl)-$C_1$-$C_6$ alkyl, $C_{3-10}$ carbocyclyl, $C_{4-10}$ (carbocyclyl)alkyl, (5 to 10 membered heterocyclyl)-$C_1$-$C_6$ alkyl, amido, and a suitable amine protecting group, provided that at least one of $R_{21}$ and $R_{22}$ is not hydrogen. In some embodiments, $R_{21}$ and $R_{22}$, together with the atoms to which they are attached, form a 5 to 10 membered heterocyclyl ring.

In some embodiments, the compounds or pharmaceutically acceptable salts thereof of Formula (Ia) may be one of the following or selected from the following group:

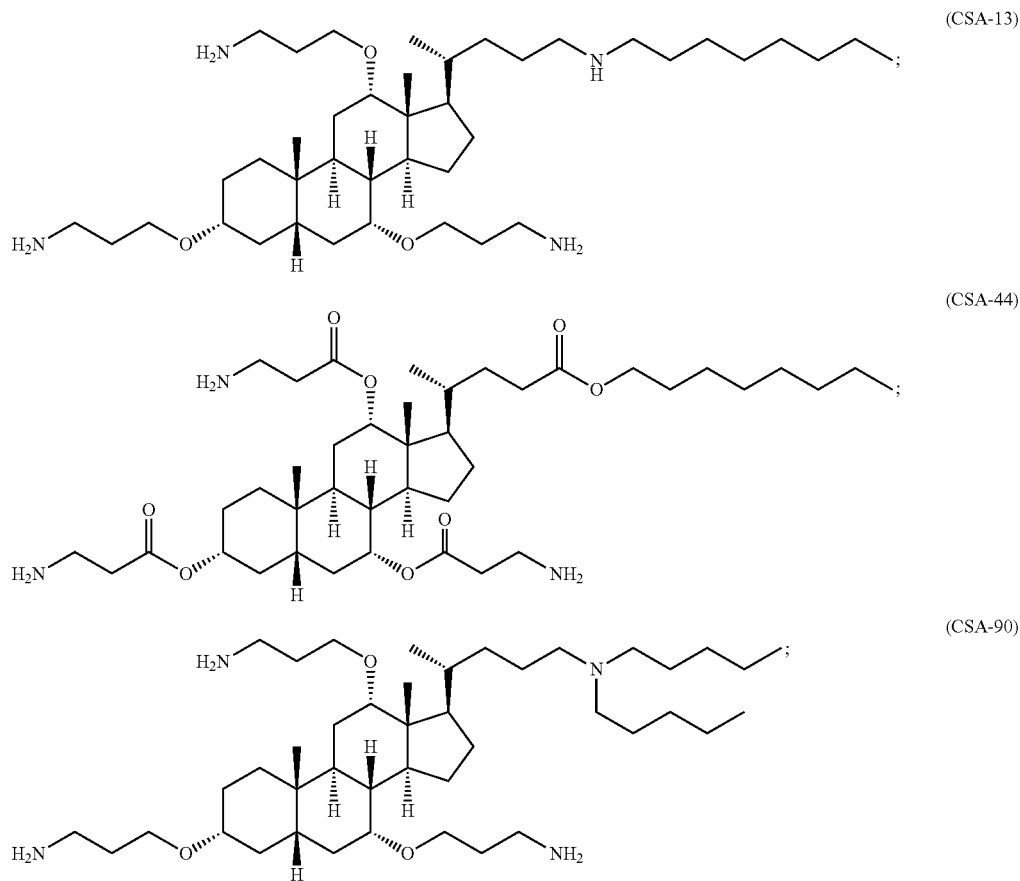

-continued

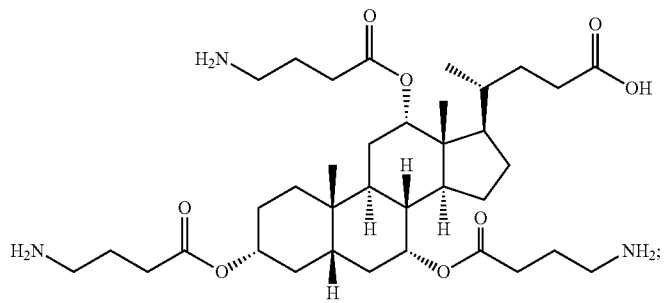
(CSA-56)

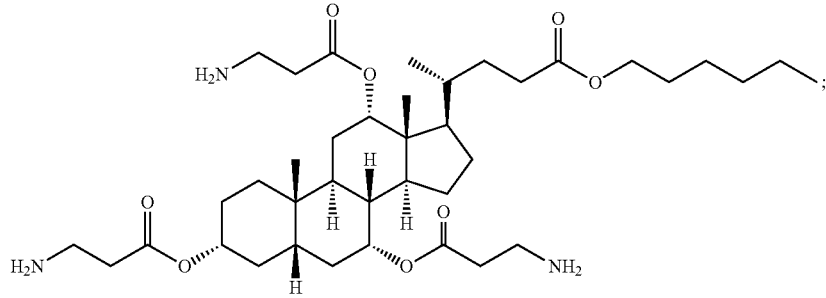
(CSA-142)

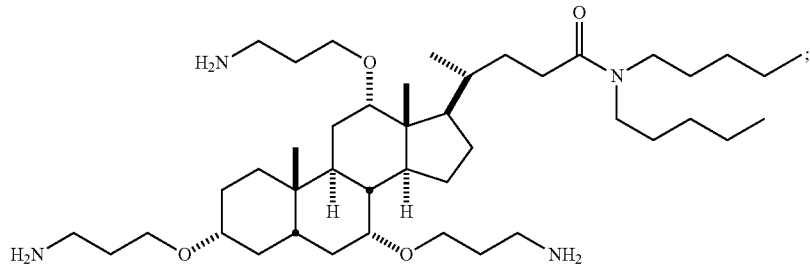
(CSA-190)

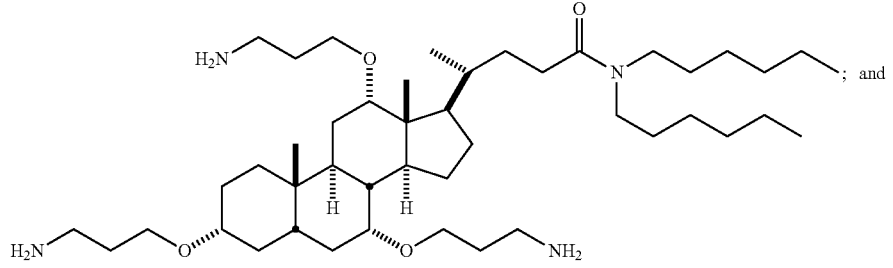
(CSA-191) ; and

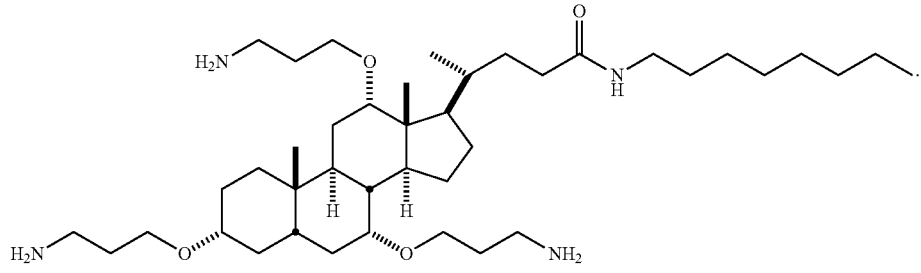
(CSA-192).

The foregoing compounds may be provided as a pharmaceutically acceptable salt such as, but not limited to, a hydrochloride salt or a tri-hydrochloride salt.

In some embodiments, compounds comprise a ring system of at least 4 fused rings, where each of the rings has from 5-7 atoms. The ring system has two faces, and contains 3 chains attached to the same face. Each of the chains contains a nitrogen-containing group that is separated from the ring system by at least one atom; the nitrogen-containing group is an amino group, e.g., a primary amino group, or a guanidino group.

The compound can also contain a hydrophobic group. In some embodiments, the hydrophobic group is a substituted $(C_{3-10})$ aminoalkyl group, a $(C_1-C_{10})$ alkyloxy $(C_{3-10})$ alkyl group, or a ($C_1$-$C_{10}$) alkylamino ($C_{3-10}$) alkyl group, attached to the steroid backbone. In some embodiments, the hydrophobic group is a substituted, branched, or unbranched substitutent with greater than 12, 16, 18, 20, or 22 carbons. In some embodiments, the hydrophobic group may include a hydrocarbon chain of at least 9, 11, or 13 carbons distal to a heteroatom. In some embodiments, a compound having a structure according to Formula (V) includes a hydrophobic group at $R^{18}$.

In some embodiments, the compounds set forth herein preserve certain stereochemical and electronic characteristics found in steroids. The term "same configuration" as used herein refers to substituents on the fused steroid having the same stereochemical orientation. For example, in some embodiments, substituents $R_3$, $R_7$ and $R_{12}$ are all β-substituted or α-substituted.

In some embodiments, compounds include, but are not limited to, compounds having amine or guanidine groups covalently attached to a steroid backbone or scaffold at any carbon position, e.g., cholic acid. In various embodiments, a group is covalently attached at any one, or more, of positions $C_3$, $C_7$ and $C_{12}$ of the steroid backbone or scaffold. In additional embodiments, a group is absent from anyone, or more, of positions $C_3$, $C_7$ and $C_{12}$ of the steroid backbone or scaffold. Compounds that include such groups can include a tether, the tether having variable chain length or size. As used herein, the terms "tether" or "tethered," when used in reference to a compound, refers to the chain of atoms between the steroid backbone or scaffold and a terminal amino or guanidine group. In various embodiments, a tether is covalently attached at anyone, or more, of positions $C_3$, $C_7$ and $C_{12}$. In additional embodiments, a tether is lacking at anyone, or more, of positions $C_3$, $C_7$ and $C_{12}$. A tether length may include the heteroatom (O or N) covalently attached to the steroid backbone. The tether may include a hydrolysable linkage such as an ester linkage.

In some embodiments, other ring systems can also be used, e.g., 5-member fused rings. Compounds with backbones having a combination of 5- and 6-membered rings are also contemplated. Amine or guanidine groups can be separated from the backbone by at least one, two, three, four or more atoms. The backbone can be used to orient the amine or guanidine groups on one face, or plane, of the steroid. For example, a scheme showing a compound having primary amino groups on one face, or plane, of a backbone is shown in Scheme I above.

The compounds and compositions disclosed herein are optionally prepared as pharmaceutically acceptable salts. The term "pharmaceutically acceptable salt" as used herein is a broad term, and is to be given its ordinary and customary meaning to a skilled artisan (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid, propionic acid, glycolic acid, pyruvic acid, malonic acid, maleic acid, fumaric acid, trifluoroacetic acid, benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, $C_1$-$C_7$ alkylamine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

The forgoing compositions may be used for the novel use of increasing the rate of wound healing in a subject with a tissue wound.

Tissue Treatment Compositions

While it is possible for the compounds described herein to be administered alone, it may be preferable to formulate the compounds as pharmaceutical compositions suitable for application to the tissue wound. As such, in yet another aspect, tissue treatment compositions useful in the methods and uses of the disclosed embodiments are provided. More particularly, the tissue treatment compositions described herein may be useful, inter alia, for treating or promoting wound healing in a subject. A tissue treatment composition is any composition that may be administered in vitro or in vivo or both to a subject in order to promote or enhance wound healing. In a preferred embodiment, a tissue treatment compositions may be administered in vivo.

As used herein the terms "pharmaceutically acceptable" and "physiologically acceptable" mean a biologically compatible formulation, gaseous, liquid or solid, or mixture thereof, which is suitable for one or more routes of administration, in vivo delivery, or contact. A formulation is compatible in that it does not destroy activity of an active ingredient therein (e.g., a CSA), or induce adverse side effects that far outweigh any prophylactic or therapeutic effect or benefit.

In an embodiment, the tissue treatment compositions may be formulated with pharmaceutically acceptable excipients such as carriers, solvents, stabilizers, adjuvants, diluents, etc., depending upon the particular mode of administration and dosage form. The tissue treatment compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5.0 to about pH 8. More particularly, the tissue treatment compositions may comprise a therapeutically or prophylactically effective amount of at least one compound as described herein, together with one or more pharmaceutically acceptable excipients. Optionally, the tissue treatment compositions may comprise a combination of the compounds described herein, or may include a second active ingredient useful in the treatment or prevention of bacterial infection (e.g., anti-bacterial or anti-microbial agents).

Formulations, e.g., for parenteral or oral administration, are most typically solids, liquid solutions, emulsions or suspensions, while inhalable formulations for pulmonary administration are generally liquids or powders, with powder formulations being generally preferred. A preferred tissue treatment composition may also be formulated as a lyophilized solid that is reconstituted with a physiologically compatible solvent prior to administration. Alternative tissue treatment compositions may be formulated as syrups, creams, ointments, tablets, and the like.

In general, formulations are prepared by uniformly and intimately associating the active ingredient with liquid carriers or finely divided solid carriers or both, and then, if necessary, shaping the product. For example, a tablet may be made by compression or molding. Compressed tablets may be prepared by compressing, in a suitable machine, an active ingredient (e.g., a CSA) in a free-flowing form such as a powder or granules, optionally mixed with a binder, lubricant, inert diluent, preservative, surface-active or dispersing agent. Molded tablets may be produced by molding, in a suitable apparatus, a mixture of powdered compound (e.g., CSA) moistened with an inert liquid diluent. The tablets may optionally be coated or scored and may be formulated so as to provide a slow or controlled release of the active ingredient therein.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

Additionally, the tissue treatment compositions may be in the form of a sterile injectable preparation, such as a sterile injectable aqueous emulsion or oleaginous suspension. This emulsion or suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, such as a solution in 1,2-propane-diol.

The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids such as oleic acid may likewise be used in the preparation of injectables.

To obtain a stable water-soluble dose form of a tissue treatment compositions, a pharmaceutically acceptable salt of a compound described herein may be dissolved in an aqueous solution of an organic or inorganic acid, such as 0.3 M solution of succinic acid, or more preferably, citric acid. If a soluble salt form is not available, the compound may be dissolved in a suitable co-solvent or combination of co-solvents. Examples of suitable co-solvents include alcohol, propylene glycol, polyethylene glycol 300, polysorbate 80, glycerin and the like in concentrations ranging from about 0 to about 60% of the total volume. In one embodiment, the active compound is dissolved in DMSO and diluted with water.

The pharmaceutical composition may also be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In one embodiment, the compounds described herein may be formulated for oral administration in a lipid-based formulation suitable for low solubility compounds. Lipid-based formulations can generally enhance the oral bioavailability of such compounds.

In some exemplary embodiments, a CSA comprises a multimer (e.g., a dimer, trimer, tetramer, or higher order polymer). In some exemplary embodiments, the CSAs can be incorporated into pharmaceutical compositions or formulations. Such compositions/formulations are useful for administration to a subject, in vivo or ex vivo. Tissue treatment compositions and formulations include carriers or excipients for administration to a subject.

Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

Additionally, it may be desirable to include other therapeutically beneficial agents in the formulation. For example, the vehicles or carriers may also include humectants or moisturizers to maintain a desired moisture level in the treated area. Other possibilities include drugs such as anesthetics or antibiotics, which provide other desired effects. Again, the possibilities are unlimited and are left to the practitioner.

A tissue treatment composition contains a total amount of the active ingredient(s) sufficient to achieve an intended therapeutic effect. In some embodiments, the tissue treatment composition includes the CSA in a weight/weight concentration of at least 0.001%, 0.01%, 0.1%, 1.0%, and/or less than 80%, 50%, 25%, 15%, 10%, or 5%, or within a range between any of the foregoing lower and upper endpoints. In some embodiments, the tissue treatment composition includes the CSA in a weight/weight concentration of about 0.04%. In other embodiments, the tissue treatment composition includes the CSA in a weight/weight concentration of less than 0.1%. In some embodiments, the tissue treatment composition includes the CSA in a weight/weight concentration of between about 0.01% and about 2.0%.

Methods and Uses

Methods disclosed herein include identifying a subject with a tissue wound and administering a tissue treatment composition including a CSA, thereby increasing the rate of wound healing. In some embodiments, the method includes (i) providing a tissue treatment composition as described above; (ii) identifying a subject in need of accelerated healing of a tissue wound; and (iii) contacting the tissue wound with the tissue treatment composition to increase the rate of healing thereof.

In some embodiments, the subject is an animal. In some embodiments, the animal is a mammal. The mammal may be a human or primate in some embodiments. A mammal includes any mammal, such as by way of non-limiting example, cattle, pigs, sheep, goats, horses, camels, buffalo, cats, dogs, rats, mice, and humans. Preferably the subject is a human, horse, or dog. In some embodiments, the subject is a vertebrate. In other embodiments, the subject is a non-human animal.

The subject has a tissue wound in need of healing and/or accelerated healing. Unless specified, the term "wound" is used herein in its generic sense, meaning that it encompasses all types of wounds and injuries. The term "wound" encompasses burns, ulcers, lacerations, incisions, etc. "Wound" and "lesion" may be used interchangeably herein, and unless the context specifically dictates otherwise, no distinction is intended. Lesions/wounds can be acute or chronic. Wounds can be full thickness, i.e., penetrating all layers of skin, or partial thickness, i.e., penetrating less than all layers of skin. Examples of acute wounds include, but are not limited to, surgical wounds (i.e., incisions), penetrating wounds, avulsion injuries, crushing injuries, shearing injuries, burn injuries, lacerations, and bite wounds. Examples of chronic wounds include, but are not limited to, ulcers, such as arterial ulcers, venous ulcers, pressure ulcers, and diabetic ulcers. Of course, acute wounds can become chronic wounds.

In some embodiments, the tissue wound can be a navel of a newborn subject (i.e., a newborn with navel ill).

The tissue treatment composition can be applied to an open wound or a closed wound. In some embodiments the composition is applied to an open wound for a period of sufficient time to cause closure of the wound. The composition can be applied at least once or twice daily at least 2, 4, 8, or 16 times and/or for over a period of at least 2, 4, 8, or 16 days.

The compositions disclosed herein can be administered to any wound, anywhere it is desirable to promote wound healing. The compositions are also useful to reduce scarring after a wound is closed and/or healed. The compositions can be applied in any form of vehicle or carrier, including but not limited to, liquids, gels, lotions, creams, pastes, and ointments. The means of application will depend upon what form the composition takes: liquids can be sprayed or poured, for example; gels, lotions, creams, pastes, and ointments can be rubbed or massaged, for example. These and other forms, and/or carriers/vehicles, for composition delivery, are described in publications such as Remington's Pharmaceutical Science, and other similar publications.

The delivery forms can be homogeneous, e.g., forms in which the composition is in solution, or heterogeneous, e.g., forms in which the composition is contained within liposomes or microspheres. The forms can produce an immediate effect, and can alternatively, or additionally, produce an extended effect. For example, liposomes, or microspheres, or other similar means of providing an extended release of the composition, can be used to extend the period during which the composition is exposed to the lesion; non-encapsulated compositions can also be provided for an immediate effect.

The delivery forms can also take the form of devices, which can deliver the composition to a lesion for a desired period of time. Devices include, but are not limited to, bandages, surgical dressings, gauzes, adhesive strips, surgical staples, clips, hemostats, intrauterine devices, sutures, trocars, catheters, tubes, collagen sponges, and implants. Implants include, but are not limited to, pills, pellets, rods, wafers, discs, and tablets.

Devices according to the disclosure can be prepared according to known methods, and can include, or be made from, polymeric material. In some instances, the polymeric material will be an absorbable material and in other instances, a non-absorbable material, or in other instances a resorbable material. Devices can include absorbable, non-absorbable, resorbable materials, and combinations thereof.

Absorbable materials can be synthetic materials and non-synthetic materials. Absorbable synthetic materials include, but are not limited to, cellulosic polymers, glycolic acid polymers, methacrylate polymers, ethylene vinyl acetate polymers, ethylene vinyl alcohol copolymers, polycaptrolactam, polyacetate, copolymers of lactide and glycolide, polydioxanone, polyglactin, poliglecaprone, polyglyconate, polygluconate, and combinations thereof. Absorbable non-synthetic materials include, but are not limited to, catgut, cargile membrane, fascia lata, gelatin, collagen, and combinations thereof.

Nonabsorbable synthetic materials include, but are not limited to nylons, rayons, polyesters, polyolefins, and combinations thereof. Non-absorbable non-synthetic materials include, but are not limited to, silk, dermal silk, cotton, linen, and combinations thereof.

Combinations of the foregoing devices and carriers/vehicles are also envisioned. For example, a CSA gel or ointment can be impregnated into a bandage or wound dressing for delivery of the CSA to the desired location. As another example, an implantable absorbable device can be loaded with a CSA solution and release the solution from the device over a period as desired.

It may be desirable to provide for other conditions in the practice of the present methods. For example, it may be desirable to ensure that the target region of the lesion is sufficiently oxygenated; generally, it is sufficient that atmospheric oxygen be present. It also may be desirable to maintain a desired level of moisture and a particular temperature; in some embodiments, a warm, moist environment is desirable. While not required, it may also be desirable to establish or maintain a sterile environment.

In some embodiments, the composition may be incorporated into a medical device coating.

One of ordinary skill in the art to which these exemplary embodiments belong will understand that the compositions may be administered in numerous ways. For example, administration may mean simply applying the compositions to a wound directly. In some exemplary embodiments, administration may be enteral, parenteral, or topical. Other exemplary routes of administration for contact or in vivo delivery which a compound can optionally be formulated include inhalation, respiration, intubation, intrapulmonary instillation, oral (buccal, sublingual, mucosal), intrapulmonary, rectal, vaginal, intrauterine, intradermal, topical, dermal, parenteral (e.g., subcutaneous, intramuscular, intravenous, intradermal, intraocular, intratracheal and epidural), intranasal, intrathecal, intraarticular, intracavity, transdermal, iontophoretic, ophthalmic, optical (e.g., corneal), intraglandular, intraorgan, intralymphatic.

Dosage

Compounds (e.g., CSAs), including pharmaceutical formulations can be packaged in unit dosage forms for ease of administration and uniformity of dosage. A "unit dosage form" as used herein refers to a physically discrete unit suited as unitary dosages for the subject to be treated; each unit containing a predetermined quantity of compound optionally in association with a pharmaceutical carrier (excipient, diluent, vehicle or filling agent) which, when administered in one or more doses, is calculated to produce a desired effect (e.g., prophylactic or therapeutic effect or benefit). Unit dosage forms can contain a daily dose or unit, daily sub-dose, or an appropriate fraction thereof, of an administered compound (e.g., CSA). Unit dosage forms also include, for example, capsules, troches, cachets, lozenges, tablets, ampules and vials, which may include a composition in a freeze-dried or lyophilized state; a sterile liquid carrier, for example, can be added prior to administration or delivery in vivo. Unit dosage forms additionally include, for example, ampules and vials with liquid compositions disposed therein. Unit dosage forms further include compounds for transdermal administration, such as "patches" that contact with the epidermis of the subject for an extended or brief period of time. The individual unit dosage forms can be included in multi-dose kits or containers. Pharmaceutical formulations can be packaged in single or multiple unit dosage forms for ease of administration and uniformity of dosage.

Compounds (e.g., CSAs) can be administered in accordance with the methods at any frequency as a single bolus or multiple dose e.g., one, two, three, four, five, or more times hourly, daily, weekly, monthly, or annually or between about 1 to 10 days, weeks, months, or for as long as appropriate. Exemplary frequencies are typically from 1-7 times, 1-5 times, 1-3 times, 2-times or once, daily, weekly or monthly. Timing of contact, administration ex vivo or in vivo delivery can be dictated by the infection, pathogenesis, symptom, pathology or adverse side effect to be treated. For example, an amount can be administered to the subject substantially contemporaneously with, or within about 1-60 minutes or hours of the onset of a symptom or adverse side effect, pathogenesis, or vaccination.

Doses may vary depending upon whether the treatment is therapeutic or prophylactic, the onset, progression, severity, frequency, duration, probability of or susceptibility of the symptom, the type pathogenesis to which treatment is directed, clinical endpoint desired, previous, simultaneous or subsequent treatments, general health, age, gender or race of the subject, bioavailability, potential adverse systemic, regional or local side effects, the presence of other disorders or diseases in the subject, and other factors that will be appreciated by the skilled artisan (e.g., medical or familial history). Dose amount, frequency or duration may be increased or reduced, as indicated by the clinical outcome desired, status of the infection, symptom or pathology, any adverse side effects of the treatment or therapy. The skilled artisan will appreciate the factors that may influence the dosage, frequency and timing required to provide an amount sufficient or effective for providing a prophylactic or therapeutic effect or benefit.

In instances where animal and/or human dosages for compounds have been established for at least some condition, those same dosages may be used, or dosages that are between about 0.1% and 500%, more preferably between about 25% and 250% of the established animal and/or human dosage. Where no animal and/or human dosage is established, as will be the case for newly-discovered pharmaceutical compositions, a suitable animal and/or human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or conditions.

From preliminary studies, it found that toxicity for CSA compounds was greatly reduced at 5 µM and lower doses. An optimal standalone dose of CSAs may be 10 µM or less at, on, or near the tissue wound, but smaller amounts may be used to minimize toxicity as needed.

Kits

Kits comprising the tissue treatment compositions and instructions for performing such methods are also disclosed. The disclosure also provides kits including compounds (e.g., CSA), combination compositions and pharmaceutical compositions/formulations thereof, packaged into a suitable packaging material. In one embodiment, a kit includes packaging material, a CSA, and instructions. In various aspects, the instructions are for administering the CSA to enhance wound healing in a subject with a tissue wound. Where the tissue treatment composition is to be sprayed, the kit may include a spray container.

The term "packaging material" refers to a physical structure housing one or more components of the kit. The packaging material can maintain the components sterilely, and can be made of material commonly used for such purposes (e.g., paper, corrugated fiber, glass, plastic, foil, ampules, vials, tubes, etc.). A kit can contain a plurality of components, e.g., two or more compounds alone or in combination with a wound healing agent or treatment or drug, optionally sterile.

A kit optionally includes a label or insert including a description of the components (type, amounts, doses, etc.), instructions for use in vitro, in vivo, or ex vivo, and any other components therein. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., floppy diskette, hard disk, ZIP disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

EXAMPLES

Example 1

A horse with a chronic non-healing oral cutaneous fistula was first treated with two prior art treatments with no success. The first treatment was with an aqueous spray of Vetericyn (0.007% hypochlorite) for a period of 7 days. The second unsuccessful treatment used Furacin Salve rubbed onto the open wound and applied daily for a period of 5 days with no appreciable improvement in wound healing. The wound was successfully treated in 7 days by spraying a composition of 0.04% CSA-44 in water to the wound once daily for 7 days. The CSA-44 compound had the following structure:

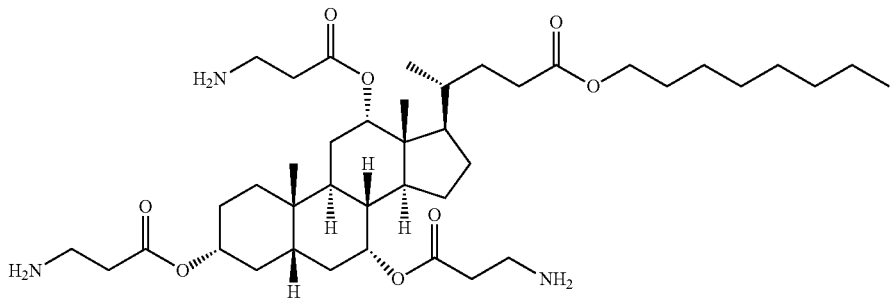

Closer of the fistula and healthy tissue were achieved in 7 days.

Example 2

A horse with a torn right front shoulder on a T post had a wound that was approximately 4 inches by 6 inches and 3 inches deep. This wound occurs commonly in horses and usually takes 3 to 6 months to heal. Typically this wound will result in a significant loss of muscle in the region. This wound was treated twice a day with a 0.04% solution of CSA-44 in water. The tissue treatment composition was applied by spraying sufficient composition to wet the entire surface of the wound. The wound closed and completely healed in 28 days without any apparent muscle loss of muscle. This result is surprising and unexpected given the location and size of wound and the typical length of time typically need for this type of wound to heal.

Example 3

A reining broodmare in Texas was involved in an accident resulting in a laceration to her left hind cannon region. The wound was 3 inches in length and 2 inches wide. The laceration extended all the way to the cannon bone, exposing the periosteum. This wound was also treated with a 0.04% solution of CSA-44 in water twice daily. No wrap was applied (i.e., no immobilization). The wound closed in 11 days with normal hair growth at 30 days. This type of wound would usually require aggressive wraps for 3 months with the possibility of other procedures being necessary for the excessive granulation tissue that commonly develops.

Example 4

A horse with an extreme case of scratches was successfully healed using CSA. Scratches is a fungal infection of the lower extremities in horses. This infection usually results in not only a fungal but also a secondary bacterial infection. In this case, the horse developed severe and debilitating granulation tissue of the ankle resulting in poor mobility due to cracking and bleeding. Prior to treatment with CSA, the wound was unsuccessfully treated with an oral antifungal, antibiotic (Naxcel), and Veterycin. The chronic infection persisted for over two years despite the multiple attempts to treat with an antimicrobial. Due to the debilitating wound the horse was slated for slaughter. However, the wound was successfully treated with a 0.04% of CSA-44 in water sprayed twice daily for four weeks. Normal hair growth and tissue was present in 4 weeks.

Example 5

A show mare developed an uncontrollable fungal infection of the skin. This malady is commonly referred to as summer itch. A 0.04% solution of CSA-44 in water was used twice daily for 3 weeks resulting in complete regrowth of normal skin and hair. Normal treatment time periods for this problem usually range from 3 to 4 months.

Example 6

Genetically diabetic 8-week-old female mice (db/db, BKS.Cg-m+/+Leprdb/J) and heterozygous nondiabetic littermates (db/−) were purchased from The Jackson Laboratory (Bar Harbor, Me.). Strain and age of mouse were chosen because these mutant mice exhibit severe diabetic conditions, with hyperglycemia peaking between 8 and 12 weeks. They have also been shown to have delayed wound healing with occlusive dressings. Mice were ordered to arrive at 7 weeks of age in order to decrease the chance of travel stress effect as a confounding factor in our experiment. Mice were housed individually in the Veteran's Affairs Medical Center—San Francisco Animal Research Facility, maintained on a 12-hour light/dark cycle, and allowed ad libitum access to rodent chow and water. Mice were anesthetized with an intraperitoneal injection of diluted chloral hydrate syrup (7½ gr/5 ml). Approximately 0.2 and 0.1 ml of a solution containing 5 ml of syrup diluted with 7 ml of ddH$_2$0 was given to each db/db and db/− mouse respectively. For each mouse, the dorsal skin was shaved, and cleansed with alcohol swabs. Mice were kept warm during anesthesia and surgery by being huddled together until they regained consciousness. Two full-thickness 6-mm punch biopsy (Acuderm, Inc., Ft. Lauderdale, Fla.) wounds were created on the dorsal surface of the mice. Wounds were placed approximately 1-2 cm apart. Areas that were chosen were free of anagen hair follicles. A piece of CSA impregnated film, approximately 6 mm in diameter, was placed in the wound. This film lay adjacent, touching the wound edges. Mastisol was applied to the edges of each wound, which was then covered with a 1×1 cm Tegaderm semiocclusive dressing. To analyze the effect of the CSA impregnated film, digital photographs of wounds, including a metric ruler, were taken on day zero and then every fourth day until complete wound closure was achieved. Prior to postoperative day 15, if Tegaderm dressing and/or impregnated film fell off, they were promptly replaced with a new dressing and/or film. On postoperative day 15, Tegaderm dressings were removed and wounds were allowed to close by contraction. On subsequent days, scabs were gently removed from the wounds not covered because they decrease the rate of wound contraction and impair assessment of wound closure. All wounds were compared to their original wound size using ImageJ (Rasband W S, NIH, http://rsb.info.nih.gov/ij/, 1997-2006).

Example 7

To determine the role of synthetic Ceragenins CSA-13, 44 and 90 in wound healing using mesenchymal stem cells (MSC), targeted mRNA panels from SABiosciences, and primary cells from Lonza were selected. Cells were purchased from Lonza.com and used fresh for each test using recommended media and culture conditions. After treatment, mRNA was isolated using Qiagen RNeasy Mini Kit®, and quantified using a NanoDrop 2000® by UV at 260 nm and 260/280 ratio for purity. cDNA was made using a First Strand Kit® from SABiosciences and processed for real time PCR using a kit from the same company for selected analysis of wound healing pathways. Results from q-PCR were uploaded to the SABiosciences site and to Ingenuity.com web site for analysis and pathway mapping. SABiosciences wound healing array plates (Cat# PAHS-121) and innate/acquired immune response plates (PAHS-052) were used. These arrays are fully validated when used as recommended. On day 1, primary human MSC cells were plated at 200,000 cells/well using 6-well plates with 3 ml of recommended media—hMSC Basal Medium+BulletKit (50 ml Growth Supplement, 10 ml L-Glutamine and 0.5 ml Gentamicin Sulfate Amphotercin-B) for 24 hours. Only early passages of cells were used, and never from frozen stock. On day 2, cells were treated with compounds dissolved in DMSO diluted 1:1000 or more to avoid effects of the solvent. Final testing concentration for CSA-13 was 5.0 µM. Treatment lasted 8 hours, and was followed by RNA isolation using QIAGEN RNeasy Mini Kit® (74104). RNA was measured at 260/280 nm using a NanoDrop 2000® and normalized to 2.4 ng per well, cDNA preparation was done using QIAGEN First Strand kit 330401. q-PCR was run as absolute quantification and threshold set at 0.1 units. Dendritic cells were plated at 500,000 cells/well using 24-well plate with 500 ul of Lonza LGM-3 Complete Growth Medium with and without compound. Treatment lasted 8 hours, and was followed by RNA isolation using QIAGEN RNeasy Mini Kit® (74104). RNA was measured at 260/280 nm using NanoDrop2000® and normalized to 2.4 ng per well, cDNA preparation was done using QIAGEN First Strand kit 330401. PCR was run as absolute quantification and threshold set at 0.1 units. For the wound healing array, strong upregulation of growth factors such as HB-EGF and cell migration factors such as MMP1 and CXCL2 were found, indicating a clear potential for CSA as a modulator of wound healing. Additional gene expression data is provided in Tables 1-3 for CSA-13, 44, and 90, respectively.

TABLE 1

Gene Expression Results for CSA-13

| Gene Symbol | Fold Regulation |
| --- | --- |
| CCL7 | 1.6632 |
| CXCL1 | 1.6181 |
| CXCL2 | 4.873 |
| CXCL5 | 2.0582 |
| F13A1 | 2.0916 |
| FGF10 | 3.8659 |

TABLE 1-continued

Gene Expression Results for CSA-13

| Gene Symbol | Fold Regulation |
| --- | --- |
| HBEGF | 3.255 |
| IL2 | 1.865 |
| IL6 | 3.1692 |
| ITGA2 | 3.5659 |
| MMP1 | 4.4172 |
| PLAU | 1.7849 |
| PLAUR | 1.6286 |
| PTGS2 | 3.3333 |
| VEGFA | 1.7274 |
| VTN | 2.0612 |
| ANGPT1 | −2.0046 |
| CSF2 | −2.4867 |
| F3 | −3.3945 |
| FGF2 | −1.633 |
| IL10 | −1.6166 |
| IL4 | −1.9944 |
| ITGB3 | −1.5243 |
| PLAT | −2.1487 |

TABLE 2

Gene Expression Results for CSA-44

| Gene Symbol | Fold Regulation |
| --- | --- |
| CCL7 | 2.1961 |
| COL1A2 | 1.5483 |
| COL3A1 | 1.7385 |
| CTSK | 1.6388 |
| CTSL2 | 1.7924 |
| CXCL2 | 14.3964 |
| EGFR | 1.5364 |
| F13A1 | 2.0963 |
| FGF10 | 2.2811 |
| FGF7 | 4.84 |
| HBEGF | 3.5463 |
| HGF | 3.1098 |
| IGF1 | 1.6877 |
| IL2 | 2.1928 |
| IL6 | 4.0387 |
| ITGA2 | 16.0648 |
| ITGB6 | 1.6323 |
| MMP1 | 68.9688 |
| MMP9 | 1.5543 |
| PLAU | 1.6131 |
| PLAUR | 2.5454 |
| PTGS2 | 48.6907 |
| TIMP1 | 1.6126 |
| VEGFA | 4.6052 |
| ACTA2 | −1.9377 |
| ANGPT1 | −2.0857 |
| CCL2 | −3.1925 |
| CDH1 | −2.7158 |
| COL4A3 | −2.4845 |
| CSF2 | −1.8551 |
| CTGF | −24.5295 |
| FGF2 | −1.6016 |
| IL10 | −2.0128 |
| ITGB3 | −1.5802 |
| PLAT | −1.754 |
| SERPINE1 | −2.9618 |
| TGFBR3 | −2.0462 |
| WISP1 | −1.9722 |
| ACTB | −1.7981 |

TABLE 3

Gene Expression Results for CSA-90

| Gene Symbol | Fold Regulation |
|---|---|
| CCL7 | 2.2874 |
| CTSK | 1.5366 |
| CTSL2 | 1.6306 |
| CXCL1 | 3.1083 |
| CXCL2 | 36.5878 |
| EGFR | 1.6212 |
| F13A1 | 2.1032 |
| FGF10 | 1.9842 |
| FGF7 | 5.1689 |
| HBEGF | 3.5988 |
| HGF | 2.3334 |
| IFNG | 1.839 |
| IGF1 | 2.2724 |
| IL2 | 1.8522 |
| IL6 | 7.2299 |
| ITGA2 | 14.3637 |
| ITGB6 | 1.9381 |
| MMP1 | 45.3753 |
| MMP9 | 2.5652 |
| PLAUR | 1.9924 |
| PTGS2 | 66.6189 |
| TIMP1 | 1.8212 |
| VEGFA | 3.3257 |
| ACTA2 | −2.5014 |
| ANGPT1 | −1.915 |
| CCL2 | −1.5793 |
| COL4A3 | −1.6195 |
| CTGF | −15.7171 |
| IL10 | −1.7382 |
| ITGA3 | −1.5127 |
| ITGB3 | −1.538 |
| PLAT | −2.14 |
| SERPINE1 | −3.7307 |
| TGFBR3 | −1.5938 |
| WISP1 | −2.3543 |
| ACTB | −2.0745 |

Example 8

Infections acquired after burn injuries in combat soldiers increase chances of sepsis and death. These burn wounds are susceptible to biofilm formation, an environment that can decrease treatment effectiveness. Most antimicrobial treatments do not target biofilms nor promote wound repair of infected wounds. Because of the lack of effects associated with current treatments, there is a need for antimicrobial agents that both promote wound healing processes in skin and eradicate polymicrobial biofilms. Our body produces antimicrobial peptides as part of the innate defense against infections. Peptides, while effective in vitro, often face degradation in the body. We hypothesize that peptides with stability modifications and peptide-mimics maintain anti-biofilm potency and induce wound healing pathways.

Standard microdilution methods were used to determine minimum inhibitory concentration (MIC) and minimum bactericidal concentration (MBC) of test agents (peptides and peptide-mimics) against drug resistant *Staphylococcus. aureus* (TCH1516) and *Pseudomonas. aeruginosa* (PAO1). Mixed-species biofilms of *S. aureus* and *P. aeruginosa*, grown in collagen-coated plates for 24 hours were tested for their susceptibility to treatments as revealed by live/dead staining. Cytotoxicity of test agents to human immortalized keratinocytes (HaCaTs) was assessed using 3-[4,5-dimethylthiazol-2-yl]-2,5-diphenyl tetrazolium bromide (MTT). Promotion of HaCaT migration by test agents was tested using electric cell-substrate impedance sensing (ECIS®), which induced 2D wound healing. The ability of test agents to stimulate angiogenesis was evaluated using matrigel-induced tube formation of human vein endothelial cells (HUVECs).

LL-37, a human peptide and positive control, showed anti-biofilm activity and induced wound healing. Ceragenins, a group of peptide-mimics, demonstrated stronger antibacterial and anti-biofilm activities, but also showed increased toxicity to HaCaTs. Dermaseptin S1 (DRS1), a frog skin peptide, increased in anti-biofilm activity when shortened to the first 15 amino acids; replacing specific residues in this sequence also affected its antibacterial and anti-biofilm activity. Preliminary studies show DRS1 peptides and ceragenins induced wound healing and angiogenesis. Through high-throughput assessment, molecules that maximize anti-biofilm potential while improving wound healing functions were down-selected for further mechanistic investigation.

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A method for increasing the rate of healing of a tissue wound, comprising:
    identifying a subject in need of accelerated healing of a tissue wound; and
    contacting the tissue wound with an effective amount of a tissue treatment composition to increase the rate of healing thereof, the tissue treatment composition comprising a cationic steroidal anti-microbial (CSA) compound of Formula V, or a pharmaceutically acceptable salt thereof, that promotes would healing and comprises a steroidal group and a plurality of cationic groups attached thereto:

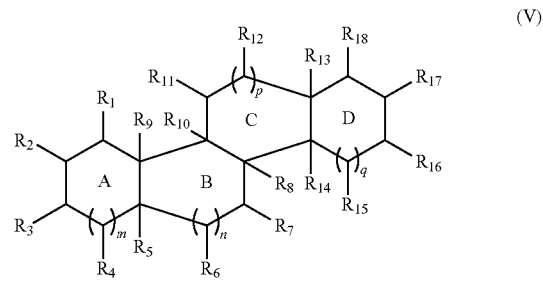

(V)

where,
rings A, B, C, and D are independently saturated, or are fully or partially unsaturated, provided that at least two of rings A, B, C, and D are saturated;
m, n, p, and q are independently 0 or 1;
$R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and substituted or unsubstituted ($C_1$-$C_6$) alkyl; and
$R_3$, $R_7$, and $R_{12}$ are independently selected from the group consisting of hydrogen, hydroxyl, substituted or unsubstituted ($C_1$-$C_{18}$) alkyl, substituted or unsubstituted ($C_1$-$C_{18}$) hydroxyalkyl, substituted or unsubstituted ($C_1$-$C_{18}$) alkyloxy-($C_1$-$C_{18}$) alkyl, substituted or unsubstituted ($C_1$-$C_{18}$) alkylcarboxy-($C_1$-$C_{18}$) alkyl, substituted or unsubstituted ($C_1$-$C_{18}$) alkylamino-($C_1$-$C_{18}$) alkyl, substituted or unsubstituted ($C_1$-$C_{18}$) alkylamino-($C_1$-$C_{18}$) alkylamino, substituted or unsubstituted ($C_1$-$C_{18}$) alkylamino-($C_1$-$C_{18}$) alkylamino-($C_1$-$C_{18}$) alkylamino, substituted or unsubstituted ($C_1$-$C_{18}$) aminoalkyl, substituted or unsubstituted aryl, substituted or unsubstituted arylamino-($C_1$-$C_{18}$) alkyl, substituted or unsubstituted ($C_1$-$C_{18}$) haloalkyl, substituted or unsubstituted ($C_2$-$C_6$) alkenyl, substituted or unsubstituted ($C_2$-$C_6$) alkynyl, oxo, linking group attached to a second CSA, substituted or unsubstituted ($C_1$-$C_{18}$) aminoalkyloxy, substituted or unsubstituted ($C_1$-$C_{18}$) aminoalkyloxy-($C_1$-$C_{18}$) alkyl, substituted or unsubstituted ($C_1$-$C_{18}$) aminoalkylcarboxy, substituted or unsubstituted ($C_1$-$C_{18}$) aminoalkylaminocarbonyl, substituted or unsubstituted ($C_1$-$C_{18}$) aminoalkylcarboxamido, substituted or unsubstituted di($C_1$-$C_{18}$ alkyl) aminoalkyl, substituted or unsubstituted C-carboxy-($C_1$-$C_{18}$) alkyl, $H_2N$—HC($Q_5$)-C(O)—O—, $H_2N$—HC($Q_5$)-C(O)—N(H)—, substituted or unsubstituted ($C_1$-$C_{18}$) azidoalkyloxy, substituted or unsubstituted ($C_1$-$C_{18}$) cyanoalkyloxy, P.G.-HN—HC($Q_5$)-C(O)—O, substituted or unsubstituted ($C_1$-$C_{18}$) guanidinoalkyloxy, substituted or unsubstituted ($C_1$-$C_{18}$) quaternary ammonium alkyl carboxy, and substituted or unsubstituted ($C_1$-$C_{18}$) guanidinoalkylcarboxy, where $Q_5$ is a side chain of an amino acid and P.G. is an amino protecting group, provided that at least two of $R_3$, $R_7$, and $R_{12}$ are not hydrogen; and $R_{18}$ is selected from the group consisting of hydroxyl, substituted or unsubstituted ($C_1$-$C_{18}$) alkyl, substituted or unsubstituted ($C_1$-$C_{18}$) hydroxyalkyl, substituted or unsubstituted ($C_1$-$C_{18}$) alkyloxy-($C_1$-$C_{18}$) alkyl, substituted or unsubstituted ($C_1$-$C_{18}$) alkylcarboxy-($C_1$-$C_{18}$) alkyl, substituted or unsubstituted ($C_1$-$C_{18}$) alkylamino-($C_1$-$C_{18}$) alkyl, substituted or unsubstituted ($C_1$-$C_{18}$) alkylamino-($C_1$-$C_{18}$) alkylamino, substituted or unsubstituted amido, substituted or unsubstituted ($C_1$-$C_{18}$) aminoalkyl, substituted or unsubstituted aryl, substituted or unsubstituted arylamino-($C_1$-$C_{18}$) alkyl, substituted or unsubstituted ($C_1$-$C_{18}$) haloalkyl, substituted or unsubstituted ($C_2$-$C_6$) alkenyl, substituted or unsubstituted ($C_2$-$C_6$) alkynyl, linking group attached to a second CSA, substituted or unsubstituted ($C_1$-$C_{18}$) aminoalkyloxy, substituted or unsubstituted ($C_1$-$C_{18}$) aminoalkyloxy-($C_1$-$C_{18}$) alkyl, substituted or unsubstituted ($C_1$-$C_{18}$) aminoalkylcarboxy ($C_1$-$C_{18}$) alkyl, substituted or unsubstituted ($C_1$-$C_{18}$) aminoalkylaminocarbonyl, substituted or unsubstituted ($C_1$-$C_{18}$) aminoalkylcarboxamido, substituted or unsubstituted di($C_1$-$C_{18}$ alkyl) aminoalkyl, substituted or unsubstituted C-carboxy-($C_1$-$C_{18}$) alkyl, $H_2N$—HC($Q_5$)-C(O)—O—, $H_2N$—HC($Q_5$)-C(O)—N(H)—, substituted or unsubstituted ($C_1$-$C_{18}$) azidoalkyloxy, substituted or unsubstituted ($C_1$-$C_{18}$) cyanoalkyloxy, P.G.-HN—HC($Q_5$)-C(O)—O, substituted or unsubstituted ($C_1$-$C_{18}$) guanidinoalkyloxy, substituted or unsubstituted ($C_1$-$C_{18}$) quaternary ammonium alkylcarboxy, and substituted or unsubstituted ($C_1$-$C_{18}$) guanidinoalkylcarboxy, where $Q_5$ is a side chain of an amino acid and P.G. is an amino protecting group.

2. The method of claim 1, wherein $R_{18}$ has the following structure:

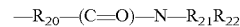

wherein,
$R_{20}$ is a substituted or unsubstituted alkyl, a substituted or unsubstituted alkenyl, a substituted or unsubstituted alkynyl, or a substituted or unsubstituted aryl; and $R_{21}$ and $R_{22}$ are independently selected from the group consisting of hydrogen, a substituted or unsubstituted $C_1$-$C_{24}$ alkyl, a substituted or unsubstituted $C_2$-$C_{24}$ alkenyl, a substituted or unsubstituted $C_2$-$C_{24}$ alkynyl, or a substituted or unsubstituted $C_6$ or $C_{10}$ aryl, 5 to 10 membered heteroaryl, 5 to 10 membered heterocyclyl, $C_{7-13}$ aralkyl, (5 to 10 membered heteroaryl)-$C_1$-$C_6$ alkyl, $C_{3-10}$ carbocyclyl, $C_{4-10}$ (carbocyclyl)alkyl, (5 to 10 membered heterocyclyl)-$C_1$-$C_6$ alkyl, amido, and an amine protecting group, provided that at least one of $R_{21}$ and $R_{22}$ is not hydrogen.

3. The method of claim 1, wherein the tissue treatment composition is applied to an open wound for a period of time sufficient to cause closure of the wound.

4. The method of claim 1, wherein the tissue treatment composition is applied to a closed wound.

5. The method of claim 1, wherein the tissue treatment composition is applied to a tissue laceration or an incision site.

6. The method of claim 1, wherein the tissue treatment composition is applied to the tissue wound in at least four separate applications and/or over a period of at least 4 days.

7. The method of claim 1, wherein the tissue treatment composition is applied to the tissue wound by spraying.

8. The method of claim 1, wherein the CSA compound is administered from a pharmaceutically acceptable device selected from the group consisting of bandages, surgical dressings, gauzes, adhesive strips, surgical staples, clips, hemostats, intrauterine devices, sutures, trocars, catheters, tubes, and implants.

9. The method of claim 1, wherein the subject is a vertebrate.

10. The method of claim 1, wherein the subject is mammal.

11. The method of claim 10, wherein the subject is a non-human mammal.

12. The method of claim 10, wherein the subject is a human, horse, or dog.

13. The method of claim 10, wherein the subject is a newborn and the tissue wound is a navel of the newborn.

14. The method of any claim 1, wherein the tissue treatment composition is for veterinary use.

15. The method of claim 1, wherein the tissue wound is a burn.

16. The method of claim 1, wherein the tissue wound is not a burn.

17. The method of claim 1, wherein the tissue wound includes a chronic infection.

18. The method of claim 1, wherein the tissue treatment composition includes the CSA in a concentration in a range between 0.01-5% wt/wt.

19. The method of claim 1, wherein the tissue treatment composition includes the CSA in a concentration in a range between about 0.01-2.0% wt/wt.

20. The method of claim 1, wherein the plurality of cationic groups are each attached to the steroidal group through a hydrolysable ester linkage.

21. The method of claim 1, wherein the CSA compound has the Formula (Ia).

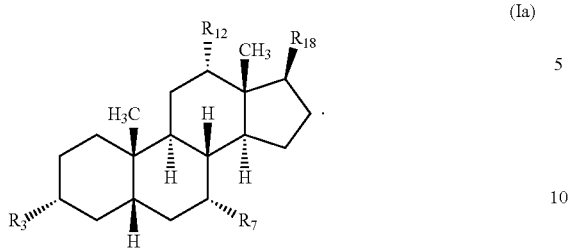

22. The method of claim 21, wherein at least $R_3$, $R_7$, and $R_{12}$ of Formula Ia are independently an aminoalkyloxy or an aminoalkylcarboxy.

23. The method of claim 21, wherein $R_{18}$ of Formula Ia is selected from the group consisting of alkylaminoalkyl, di(alkyl)aminoalkyl, alkoxycarbonylalkyl, alkylcarboxyalkyl, C-carboxyalkyl, and alkylcarbonyloxyalkyl.

24. The method of claim 21, wherein $R_{18}$ has the following structure:

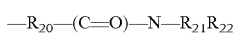

wherein, $R_{20}$ is a substituted or unsubstituted alkyl, a substituted or unsubstituted alkenyl, a substituted or unsubstituted alkynyl, or a substituted or unsubstituted aryl; and $R_{21}$ and $R_{22}$ are independently selected from the group consisting of hydrogen, a substituted or unsubstituted $C_1$-$C_{24}$ alkyl, a substituted or unsubstituted $C_2$-$C_{24}$ alkenyl, a substituted or unsubstituted $C_2$-$C_{24}$ alkynyl, or a substituted or unsubstituted $C_6$ or $C_{10}$ aryl, 5 to 10 membered heteroaryl, 5 to 10 membered heterocyclyl, $C_{7-13}$ aralkyl, (5 to 10 membered heteroaryl)-$C_1$-$C_6$ alkyl, $C_{3-10}$ carbocyclyl, $C_{4-10}$ (carbocyclyl)alkyl, (5 to 10 membered heterocyclyl)-$C_1$-$C_6$ alkyl, amido, and an amine protecting group, provided that at least one of $R_{21}$ and $R_{22}$ is not hydrogen.

25. The method of claim 1, wherein the CSA compound, or a pharmaceutically acceptable salt thereof, is selected from the group consisting of:

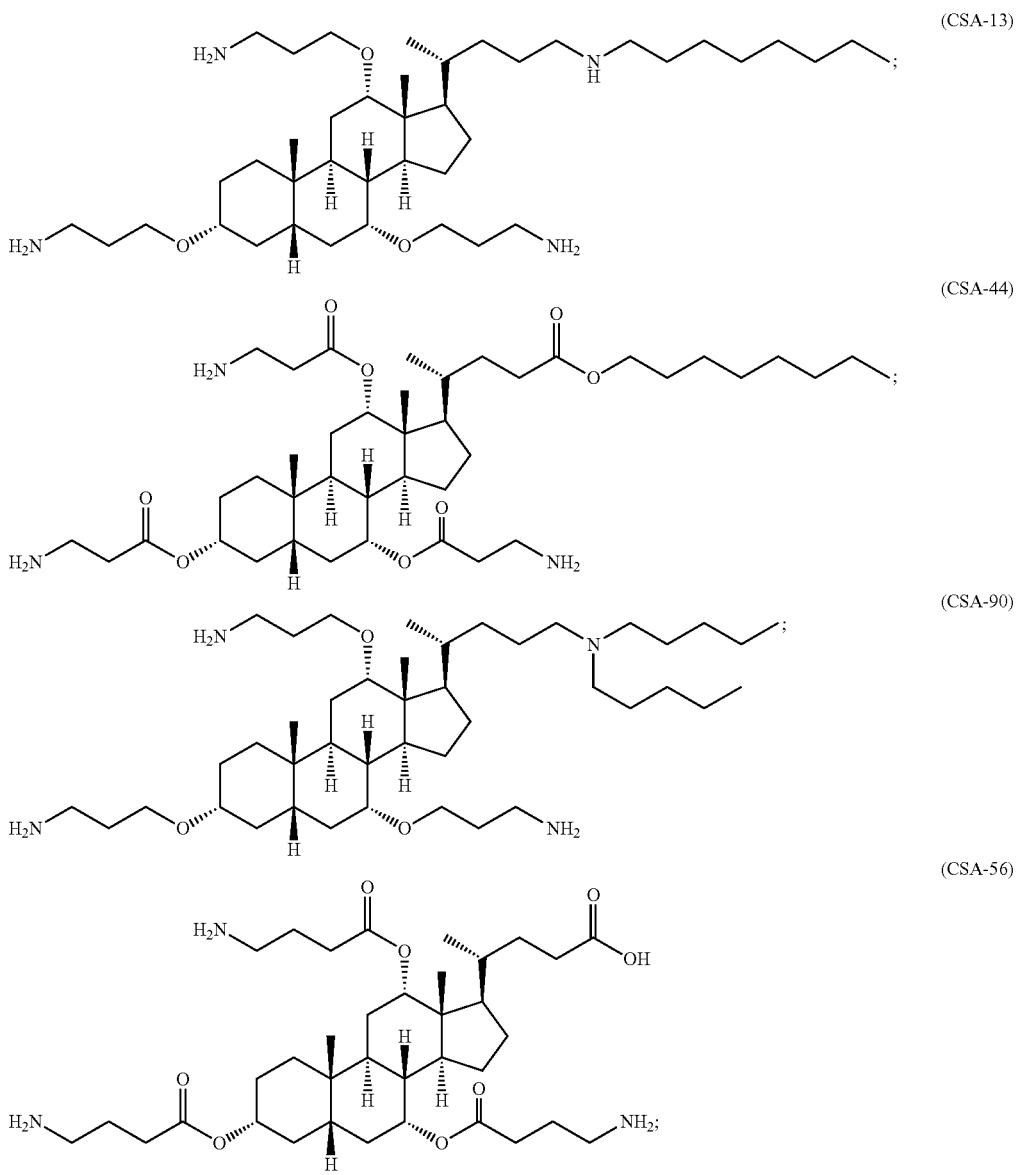

(CSA-142)
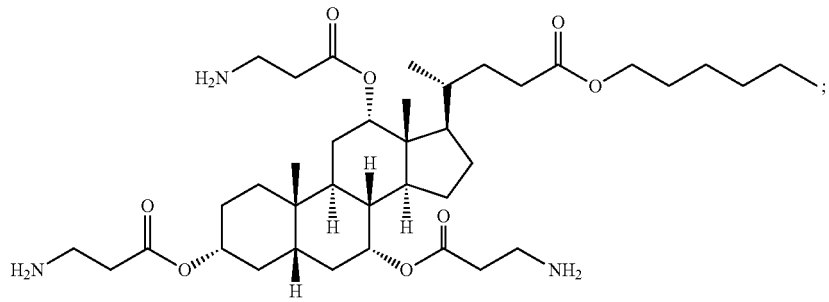
(CSA-190)
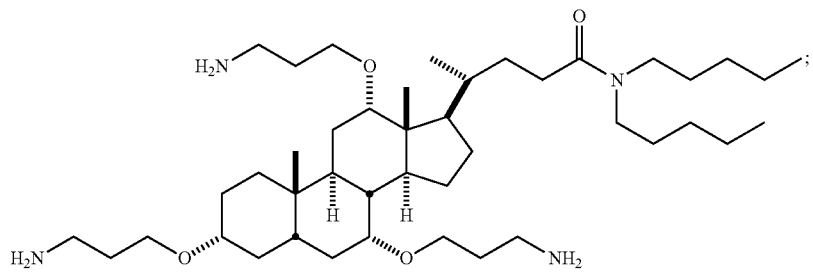
(CSA-191)
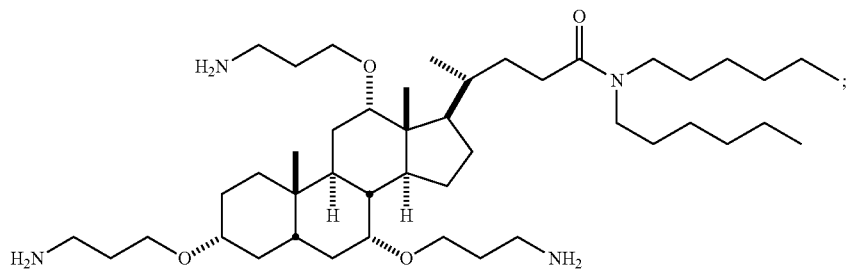
(CSA-192)
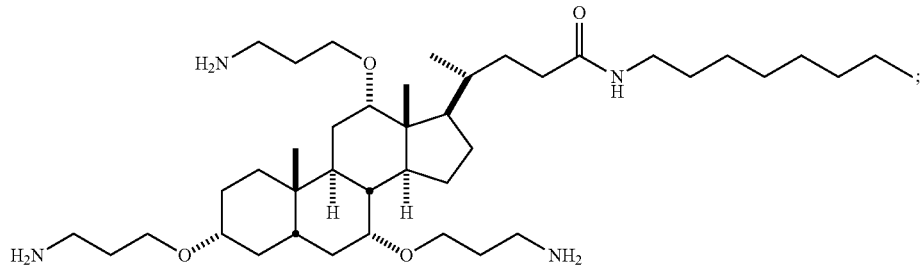
pharmaceutically acceptable salts thereof.
26. The method of claim 1, wherein the CSA compound, or a pharmaceutically acceptable salt thereof, is:
(CSA-192)
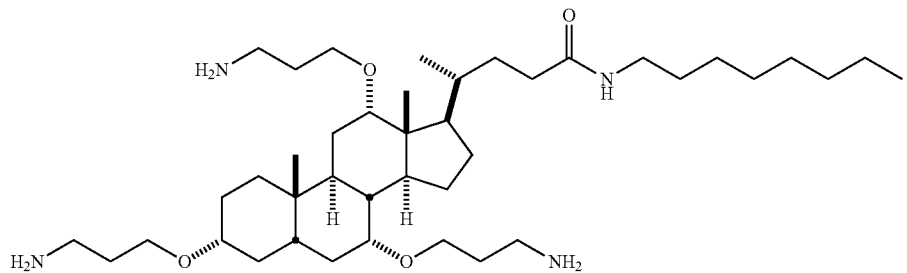
or a pharmaceutically acceptable salt thereof.

27. A method of increasing the rate of healing of a tissue wound, comprising:
identifying a subject in need of accelerated healing of a tissue wound; and
contacting the tissue wound with an effective amount of a tissue treatment composition to increase the rate of healing thereof, the tissue treatment composition comprising a cationic steroidal anti-microbial (CSA) compound of Formula Ia or pharmaceutically acceptable salt thereof that promotes wound healing:

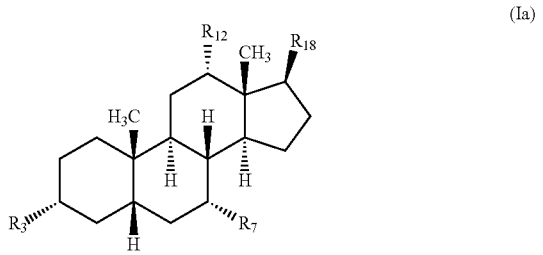

wherein,
$R_3$, $R_7$, and $R_{12}$ are independently selected from the group consisting of independently selected from the group consisting of hydrogen, an unsubstituted ($C_1$-$C_{22}$) alkyl, unsubstituted ($C_1$-$C_{22}$) hydroxyalkyl, unsubstituted ($C_1$-$C_{22}$) alkyloxy-($C_1$-$C_{22}$) alkyl, unsubstituted ($C_1$-$C_{22}$) alkylcarboxy-($C_1$-$C_{22}$) alkyl, unsubstituted ($C_1$-$C_{22}$) alkylamino-($C_1$-$C_{22}$)alkyl, unsubstituted ($C_1$-$C_{22}$) alkylamino-($C_1$-$C_{22}$) alkylamino, unsubstituted ($C_1$-$C_{22}$) alkylamino-($C_1$-$C_{22}$) alkylamino-($C_1$-$C_{18}$) alkylamino, an unsubstituted ($C_1$-$C_{22}$) aminoalkyl, an unsubstituted arylamino-($C_1$-$C_{27}$) alkyl, an unsubstituted ($C_1$-$C_{22}$) aminoalkyloxy, an unsubstituted ($C_1$-$C_{22}$) aminoalkyloxy-($C_1$-$C_{22}$) alkyl, an unsubstituted ($C_1$-$C_{22}$) aminoalkylcarboxy, an unsubstituted ($C_1$-$C_{22}$) aminoalkyl-aminocarbonyl, an unsubstituted ($C_1$-$C_{22}$) aminoalkylcarboxamido, an unsubstituted di($C_1$-$C_{22}$ alkyl)aminoalkyl, unsubstituted ($C_1$-$C_{22}$) guanidinoalkyloxy, unsubstituted ($C_1$-$C_{22}$) quaternary ammonium alkylcarboxy, and unsubstituted ($C_1$-$C_{22}$) guanidinoalkyl carboxy, provided that at least two of $R_3$, $R_7$, and $R_{12}$ are not hydrogen; and
$R_{18}$ is selected from the group consisting of substituted or unsubstituted ($C_1$-$C_{18}$) alkyl carboxy-($C_1$-$C_{18}$) alkyl, substituted or unsubstituted ($C_1$-$C_{18}$) alkylamino-($C_1$-$C_{18}$) alkyl, substituted or unsubstituted amido, substituted or unsubstituted ($C_1$-$C_{18}$) aminoalkyl, linking group attached to a second CSA, substituted or unsubstituted ($C_1$-$C_{18}$) aminoalkyloxy, substituted or unsubstituted ($C_1$-$C_{18}$) aminoalkyloxy-($C_1$-$C_{18}$) alkyl, substituted or unsubstituted ($C_1$-$C_{18}$) aminoalkylcarboxy ($C_1$-$C_{18}$) alkyl, and substituted or unsubstituted is alkyl) aminoalkyl.

28. The method of claim 27, wherein Rig has the following structure:

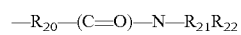

wherein,
$R_{20}$ is omitted or a substituted or unsubstituted alkyl, alkenyl, alkynyl, or aryl; and
$R_{21}$ and $R_{22}$ are independently selected from the group consisting of hydrogen, a substituted or unsubstituted alkyl, a substituted or unsubstituted alkenyl, a substituted or unsubstituted alkynyl, or a substituted or unsubstituted aryl, provided that at least one of $R_{21}$ and $R_{22}$ is not hydrogen.

29. A method of increasing the rate of healing of a tissue wound, comprising:
identifying a subject in need of accelerated healing of a tissue wound; and
contacting the tissue wound with an effective amount of a cationic steroidal anti-microbial (CSA) compound, or a pharmaceutically acceptable salt thereof, selected from the group consisting of:

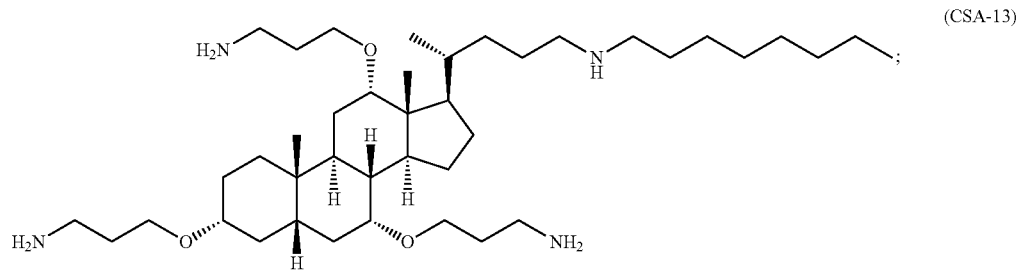

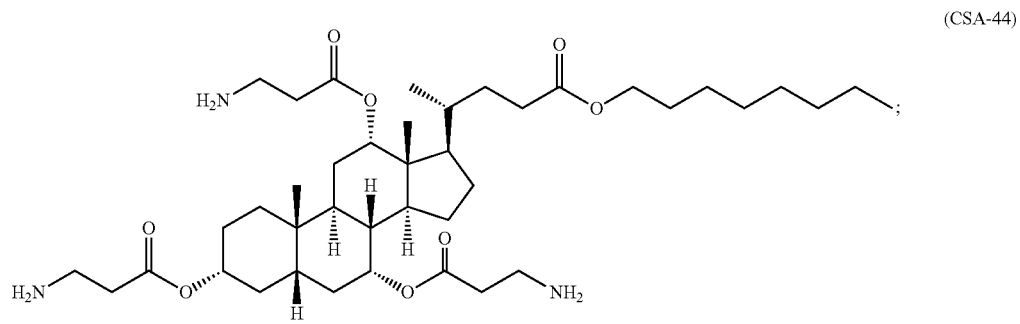

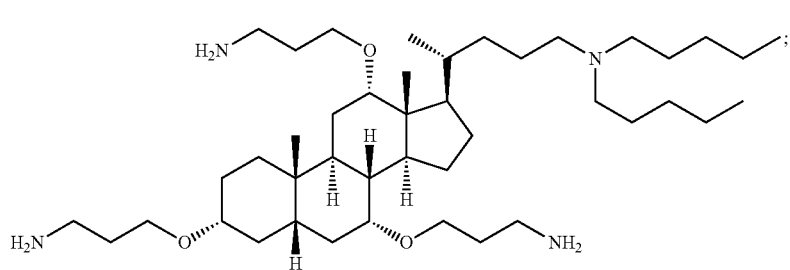
(CSA-90)
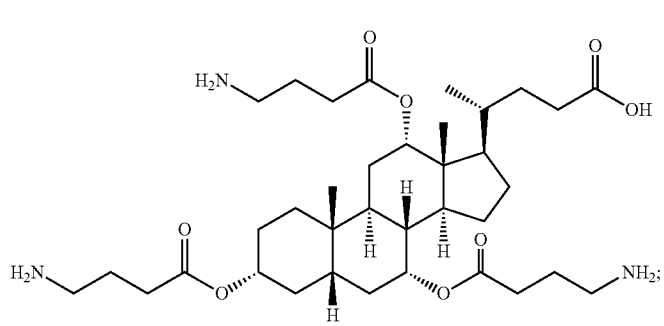
(CSA-56)
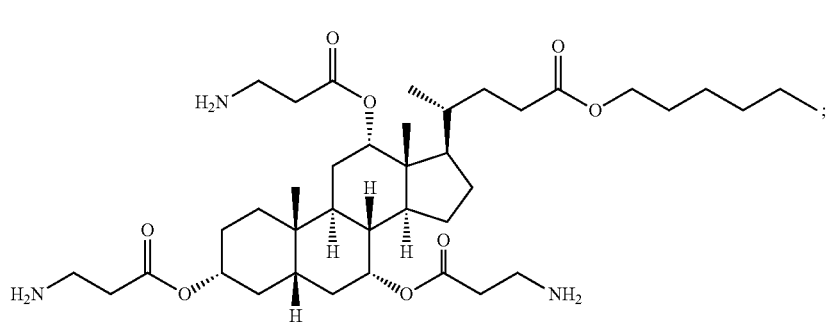
(CSA-142)
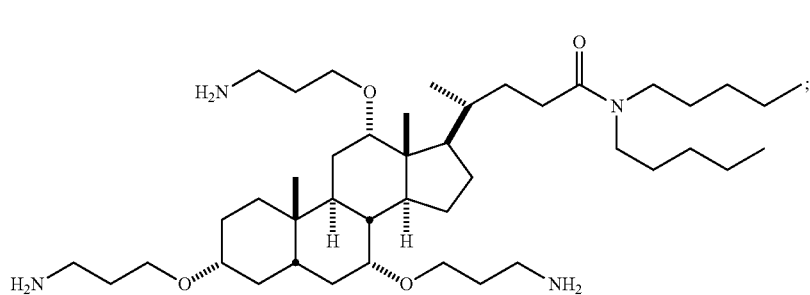
(CSA-190)
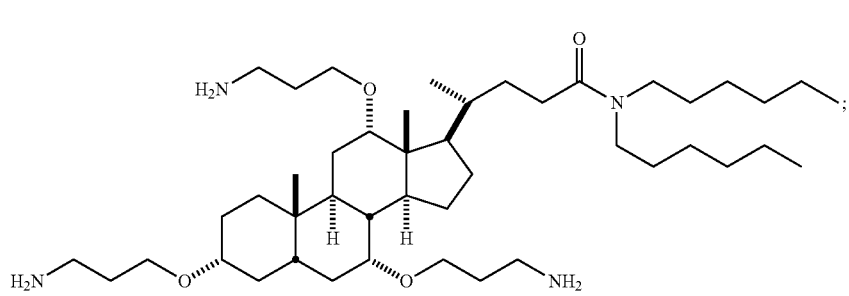
(CSA-191)

-continued
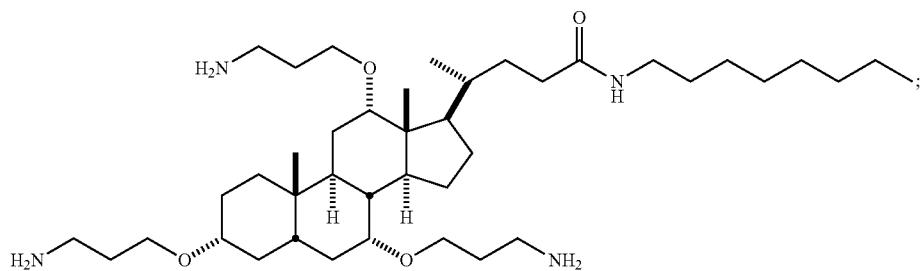
(CSA-192)
pharmaceutically acceptable salts thereof.